(12) United States Patent
Shiba et al.

(10) Patent No.: US 11,357,399 B2
(45) Date of Patent: Jun. 14, 2022

(54) OCT APPARATUS

(71) Applicant: NIDEK CO., LTD., Aichi (JP)

(72) Inventors: Ryosuke Shiba, Aichi (JP); Masaaki Hanebuchi, Aichi (JP); Naoki Takeno, Aichi (JP); Yoshiki Kumagai, Aichi (JP)

(73) Assignee: NIDEK CO., LTD., Aichi (JP)

( * ) Notice: Subject to any disclaimer, the term of this patent is extended or adjusted under 35 U.S.C. 154(b) by 262 days.

(21) Appl. No.: 16/527,527

(22) Filed: Jul. 31, 2019

(65) Prior Publication Data

US 2020/0037872 A1 Feb. 6, 2020

(30) Foreign Application Priority Data

Aug. 2, 2018 (JP) .............................. JP2018-145917
Jan. 30, 2019 (JP) .............................. JP2019-014771

(51) Int. Cl.
*A61B 3/10* (2006.01)
*A61B 3/00* (2006.01)
(Continued)

(52) U.S. Cl.
CPC .............. *A61B 3/102* (2013.01); *A61B 3/0058* (2013.01); *A61B 3/1225* (2013.01); *G06T 11/008* (2013.01); *G06T 2211/404* (2013.01)

(58) Field of Classification Search
CPC ..... A61B 3/102; A61B 3/0058; A61B 3/1225; A61B 3/0025; A61B 3/0041; A61B 3/12;
(Continued)

(56) References Cited

U.S. PATENT DOCUMENTS 10,478,059 B2 * 11/2019 Fukasawa .......... G01B 9/02004
2008/0100612 A1 5/2008 Dastmalchi et al.
(Continued)

FOREIGN PATENT DOCUMENTS

JP 2015-506772 A 3/2015

OTHER PUBLICATIONS

M. Wojtkowski, et al., "Full range complex spectral optical coherence tomography technique in eye imaging", Optics Letters, vol. 27, No. 16, Aug. 15, 2002, pp. 1415-1417.
(Continued)

*Primary Examiner* — Mohammed A Hasan
(74) *Attorney, Agent, or Firm* — Sughrue Mion, PLLC

(57) ABSTRACT

An OCT apparatus includes an OCT optical system that has a light splitter splitting light from an OCT light source to light travelling to a measurement light path and light travelling to a reference light path and a detector detecting a spectrum interference signal of measurement light guided to a subject eye through the measurement light path and reference light from the reference light path, and a processing unit that processes the spectrum interference signal to generate OCT data. The processing unit performs at least complementary processing on an overlapping region of a real image and a virtual image in OCT data based on a plurality of OCT data obtained with different optical path lengths when detecting the spectrum interference signal, and generates OCT data subjected to the complementary processing.

8 Claims, 14 Drawing Sheets

(51) Int. Cl.
*A61B 3/12* (2006.01)
*G06T 11/00* (2006.01)

(58) Field of Classification Search
CPC ............. G06T 11/008; G06T 2211/404; G01B 9/02064; G01B 9/02044; G01B 9/02078; G01B 9/02091
USPC ........................................................ 351/206
See application file for complete search history.

(56) References Cited

U.S. PATENT DOCUMENTS

| | | |
|---|---|---|
| 2009/0168017 A1 | 7/2009 | O'Hara et al. |
| 2013/0166239 A1* | 6/2013 | Ota .......................... G06F 17/14 702/70 |
| 2013/0208240 A1 | 8/2013 | Sharma et al. |
| 2018/0289256 A1* | 10/2018 | Murata ................ A61B 3/1225 |
| 2018/0360310 A1* | 12/2018 | Berlin ...................... A61B 3/13 |

OTHER PUBLICATIONS

Communication dated Jan. 9, 2020, from the European Patent Office in counterpart European Application No. 19189733.9.
Rainer A. Leitgeb et al. "Phase-shifting algorithm to achieve high-speed long-depth-range probing by frequency-domain optical coherence tomography" Optics Letters, vol. 28, No. 22, Nov. 15, 2003, (pp. 2201-2203) XP-002388372.

* cited by examiner

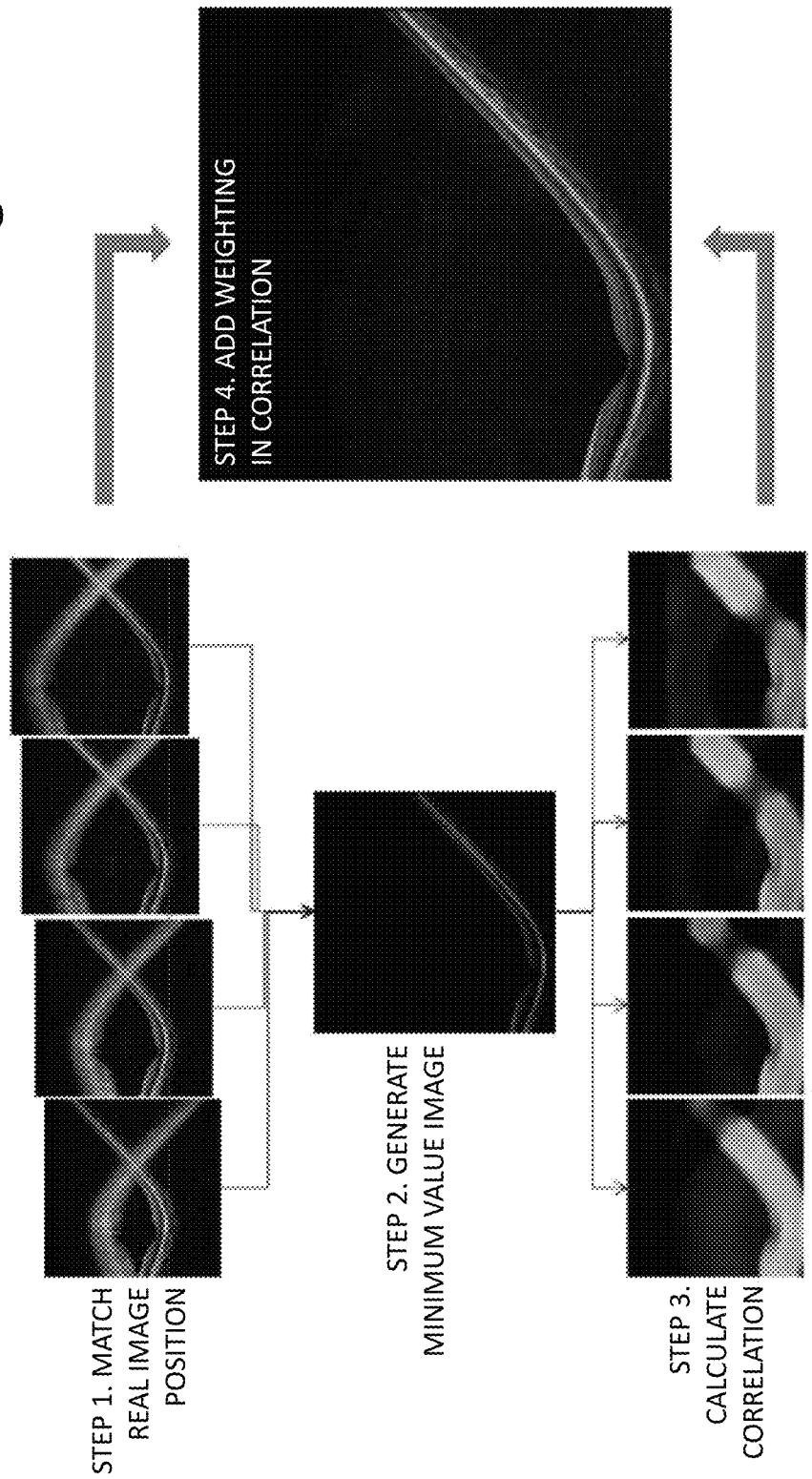

OCT APPARATUS

CROSS-REFERENCE TO RELATED APPLICATION

This application claims priority from Japanese Patent Applications No. 2018-145917 filed on Aug. 2, 2018 and No. 2019-014771 filed on Jan. 30, 2019, the entire subject-matter of which is incorporated herein by reference.

TECHNICAL FIELD

The present disclosure relates to an OCT apparatus that obtains OCT data of a subject eye.

BACKGROUND

For example, an apparatus that can acquire OCT data by processing a spectrum interference signal output from an OCT optical system is known as an OCT apparatus that obtains OCT data of a subject eye.

However, a full-range technique of removing a virtual image (also referred to as a mirror image) by using additional hardware is known as a technique for obtaining a wide range of OCT data (see, for example, Non-Patent Document 1 below).

Non-patent document 1: Wojtkowski, M. et al. (2002) Full range complex spectral optical coherence tomography technique in eye imaging, Optics Letters, 27 (16), p. 1415.

Meanwhile, JP-A-2015-506772 discloses a technique of correcting by using software without using additional hardware, at least one tissue surface extending on both sides of a zero delay position is segmented, and a virtual image is selectively removed by using the segmented tissue surface.

However, in case of a configuration described in the above-described JP-A-2015-506772, even if the virtual image is selectively removed, OCT data by the virtual image remains in a real image in a region where the real image and the virtual image overlap, and thus, it may be difficult for an examiner to perform observation, diagnose, analysis, and the like.

SUMMARY

An object of the present disclosure is to provide an OCT apparatus that can acquire a wide range of good OCT data with a simple configuration.

The OCT apparatus and the OCT image processing program according to the present disclosure have the following configuration.

There is provided an OCT apparatus including:

an OCT optical system that has a light splitter splitting light from an OCT light source to light travelling a measurement light path and light travelling to a reference light path, and a detector detecting a spectrum interference signal of measurement light guided to a subject eye through the measurement light path and reference light from the reference light path; and a processor that processes the spectrum interference signal to generate OCT data, in which the processor performs at least complementary processing on an overlapping region of a real image and a virtual image in OCT data based on a plurality of OCT data obtained with different optical path lengths when detecting the spectrum interference signal, and generates OCT data subjected to the complementary processing.

According to the present disclosure, a wide range of good OCT data can be acquired with a simple configuration.

BRIEF DESCRIPTION OF DRAWINGS

FIG. 14 is a diagram illustrating the example, which includes a progress, of the processing for detecting and erasing the virtual image M.

DETAILED DESCRIPTION

Figure 1:
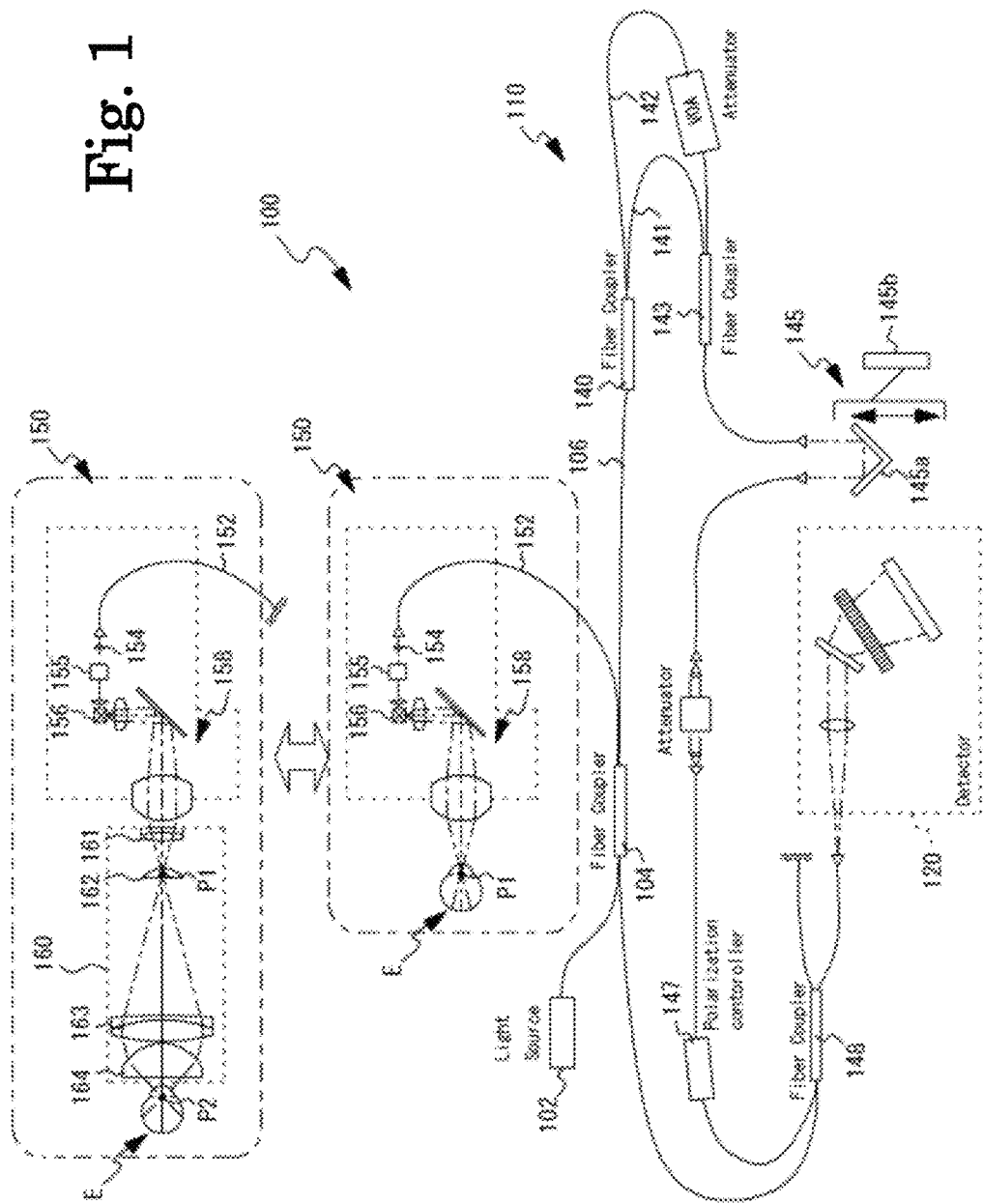
FIG. 1 is a diagram illustrating an example of an optical system of an OCT apparatus according to the present embodiment.

An example of an embodiment according to the present disclosure will be described with reference to the drawings. FIGS. 1 to 10 are diagrams relating to examples of the present embodiment. Items categorized by < > below can be used independently or in association with each other.

An OCT apparatus according to the embodiment may include an OCT optical system and may be capable of processing a spectral interference signal output from a detector of the OCT optical system and acquiring OCT data. In this case, the OCT optical system may be a Fourier domain OCT optical system (an SS-OCT optical system or an SD-OCT optical system), for example. The OCT optical system may have a light splitter for splitting light from an OCT light source to light traveling to a measurement light path and light traveling to a reference light path and may detect the spectral interference signal of measurement light guided via the measurement light path to a subject and reference light from the reference light path.

An OCT optical system may include an optical scanning unit. The optical scanning unit may be provided for scanning measurement light guided to a subject eye on the subject eye. The OCT optical system is not limited to a configuration including the optical scanning unit, and a full field OCT optical system may be used.

In addition, the OCT apparatus may include an image processor, and the image processor may be capable of processing a spectral interference signal output from the OCT optical system and acquiring the OCT data.

<Wide-Angle Imaging of Fundus>

For example, the OCT optical system may have a light splitter, which splits light from an OCT light source to light traveling to the measurement light path and light traveling to the reference light path, and a detector, which detects an interference signal of the measurement light guided to a fundus of a subject eye via the measurement light path and the reference light from the reference light path.

The OCT optical system may be an OCT optical system that is capable of guiding the measurement light to a wide-angle region. The wide-angle region includes a center area (fundus center area) and a peripheral area (fundus peripheral area) of the fundus in one transverse direction in which the measurement light traverses the fundus. For example, in a case where the measurement light traverses the fundus in a specific transverse direction (for example, a horizontal direction), the wide-angle region may a region at a wide angle so as to traverse both of the fundus center area and the fundus peripheral area. In addition, regarding a transverse region that the measurement light traverses, a transverse region in the fundus center area and a transverse region in the fundus peripheral area may be continuous to each other in the transverse direction, for example. For example, a region having a length of 18 mm or longer on the fundus may be set as the wide-angle region. It is needless to say that the wide-angle region may be used in a case of obtaining a region narrower than 18 mm. The apparatus of the embodiment is used particularly in a case of imaging a peripheral region of a subject eye of which a fundus has a large degree of curvature.

For example, at least a region including a macular region and an optic nerve head of the fundus may be set as the fundus center area, and a region including both regions on outer sides from both end portions of the fundus center area in one transverse direction may be set as the fundus peripheral area. It is needless to say that setting is not limited to this, and at least a region including the macular region of the fundus may be set as the fundus center area, and a region including both regions on outer sides from both end portions of the fundus center area in one transverse direction may be set as the fundus peripheral area, for example.

For example, the OCT optical system that is capable of guiding the measurement light to the wide-angle region of the fundus may include an objective lens optical system or may include an objective mirror optical system using a concave mirror. In addition, in the OCT optical system, an attachment optical system may be attached to (inserted into) the objective lens optical system.

<Switching of Display States>

An OCT apparatus may include a controller as a control unit. The controller may be, for example, a controller that can output OCT data obtained based on a spectrum interference signal to a display unit. In addition, the controller may control an OCT optical system and obtain the OCT data, for example.

As imaging modes for obtaining the OCT data, a first imaging mode for obtaining the OCT data on a fundus center area of the subject eye and a second imaging mode for obtaining the OCT data on a wide-angle region including the fundus center area and a fundus peripheral area of the subject eye, may be set.

The controller may switch the display state of the display unit between the first imaging mode for obtaining the OCT data on the fundus center area and the second imaging mode for obtaining the OCT data on the wide-angle region including the fundus center area and the fundus peripheral area. In this way, it is possible to easily observe the OCT data on the wide-angle region.

When switching the display state, the controller may change an output range of the OCT data on the screen of the display unit (refer to, for example, FIGS. 3A, 3B, 4A and 4B). For example, in a case where the first imaging mode is set, the controller outputs OCT data of any one of the front and rear image areas with respect to the zero delay position on the OCT data may be output to the display unit, and in a case where the second imaging mode is set, the controller outputs either of the front and rear image areas with respect to the zero delay position on the OCT data may be output to the display unit. In this way, the OCT data on the fundus center area and the OCT data on the wide-angle region can be appropriately observed, respectively. Of course, not limited to the above, for example, when the mode is set as the first imaging mode, the entire front or rear image area with respect to the zero delay position on the OCT data may be output to the display unit, and when the mode is set as the second imaging mode, both the front and rear image areas with respect to the zero delay position on the OCT data may be output to the display unit.

In the case where the controller outputs both the front and rear image areas with respect to the zero delay position on the OCT data are output to the display unit, the controller may display the OCT data including both a real image and a virtual image on the display unit. In this case, after processing for removing any one of the real image and the virtual image is performed, one of the images may be displayed on the display unit.

The controller may synthesize the OCT data on the fundus center area acquired in the first imaging mode and the OCT data on the wide-angle region including the fundus center area and the fundus peripheral area acquired in the second imaging mode, and then, may display the composite OCT data on the display unit. According to this, since the image quality of OCT data of the fundus center area in the OCT data on the wide-angle region can be improved, it is possible to achieve a more accurate observation.

The switching of the mode between the first imaging mode and the second imaging mode may be performed by a manual operation of an examiner or may be automatically performed. Furthermore, the controller may switch the display state of the display unit according to the switching of the imaging mode.

For example, the controller may switch the display state of the display unit according to switching of the imaging mode by insertion and retraction of a wide-angle attachment to the OCT optical system. In addition, according to the switching of the imaging mode by changing the scanning range of the measurement light onto the fundus, the display state of the display unit may be switched.

For example, if the scanning range of the measurement light onto the fundus is within a predetermined range, the controller may be set to the first imaging mode, and if the scanning range of the measurement light onto the fundus exceeds the predetermined range, may be set to the second imaging mode. The controller may switch the output range of the OCT data to the screen of the display unit with the mode switching signal of imaging mode as a trigger.

In this way, it is possible to smoothly perform the switching of the display state of the display unit according to the imaging mode. It is possible to smoothly perform the observation of each OCT data.

In the description above, the display state of the display unit is switched in accordance with the imaging mode, but not limited thereto. For example, the controller may be able to switch a mode between a first display mode in which the controller outputs any one of the front and rear image areas with respect to the zero delay position on the OCT data is output to the display unit and a second display mode in which the controller outputs both the front and rear image areas with respect to the zero delay position on the OCT data is output to the display unit. In switching the mode between the first display mode and the second display mode, a method similar to the method of switching the mode between the first imaging mode and the second imaging mode may be used. In addition, a switching method described in the example described later may be used.

<Dispersion Correction by Software>

The OCT apparatus may include a storage unit. For example, the storage unit may be a storage unit for storing dispersion correction data for correcting the dispersion in the OCT data. The controller may correct the spectrum interference signal using the dispersion correction data obtained from the storage unit, and may perform a Fourier analysis of the corrected spectrum interference signal to acquire the OCT data. In this way, it is possible to distinguish the real image and the virtual image, even when both the front and rear image areas with respect to the zero delay position are output to the display unit, it is possible to easily perform the observation of the OCT data.

<Analysis Processing>

The OCT apparatus may include an analysis processing unit. The analysis processing unit may be, for example, an analysis processing unit which analyzes the OCT data to obtain an analysis result. The controller described above may serve as the analysis processing unit, or the analysis processing unit may be separately provided from the controller.

When analyzing the OCT data obtained in the first imaging mode, the analysis processing unit may acquire the analysis result by analyzing any one of the front and rear image areas with respect to the zero delay position on the OCT data. When analyzing the OCT data acquired in the second imaging mode, the analysis processing unit may acquire the analysis result by analyzing both the front and rear image areas with respect to the zero delay position on the OCT data. In this way, it is possible to perform the analysis processing according to the imaging mode of the acquired OCT data.

<Complementary Processing for Overlapping Regions of Real Image and Virtual Image>

An OCT apparatus may include an image processor. The image processor may process a spectrum interference signal to generate OCT data. A control unit described above may also serve as the image processor, or the image processor may be provided separately from the control unit. Further, the present embodiment may be applied as an ophthalmic image processing program.

For example, based on a plurality of OCT data obtained with different optical path lengths when detecting a spectrum interference signal, the image processor may perform at least complementary processing for an overlapping region of a real image and a virtual image in the OCT data and generate the OCT data for which the complementary processing is performed (see, for example, FIGS. 5 to 10).

According to this, for example, good OCT data is obtained in a region where the real image and the virtual image overlap each other. Thus, a wide range of good OCT data can be acquired with a simple configuration. The complementary processing according to the present embodiment is effective, for example, when a wide range of the OCT data spanning a zero delay position is displayed. Overlap between the real image and the virtual image occurs at and near the zero delay position on the OCT data when a tissue (for example, a fundus) having reflection scattering characteristics is disposed at the zero delay position. That is, as the complementary processing according to the present embodiment is performed for the OCT data in which the overlap between the real image and the virtual image occurs, the OCT data including a region corresponding to the zero delay position can be acquired satisfactorily.

The complementary processing according to the present embodiment can be applied to, for example, the OCT data on a wide-angle region including a fundus center area and a fundus peripheral area and can acquire fundus OCT data in a good wide-angle region with a simple configuration. Further, the complementary processing according to the present embodiment can be applied to front eye portion OCT data of a wide range including a cornea region and a crystalline lens region, and the good front eye portion OCT data of a wide range can be acquired with a simple configuration.

<Complementary Processing>

Figure 10:
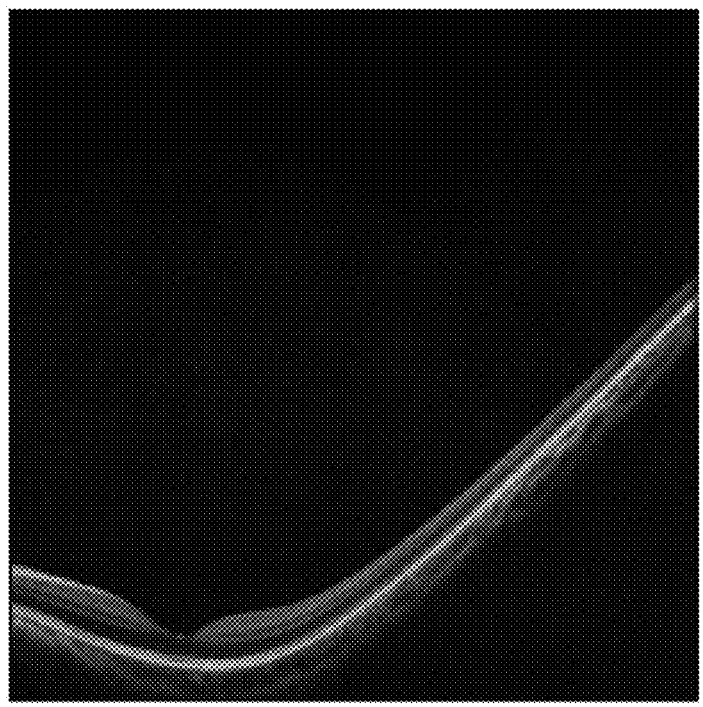
FIG. 10 is a diagram illustrating an example in a case where addition average OCT data is acquired based on each OCT data.

For example, the image processor may generate combined OCT data based on a representative value of a plurality of OCT data obtained with different optical path lengths as complementary processing (see, for example, FIG. 10). According to this, for example, good OCT data can be obtained in the entire data, and highly reliable OCT data can be obtained even for a region where a real image and a virtual image overlap each other. Further, according to processing of obtaining the representative value, it is also possible to reduce the virtual image included in the OCT data.

In this case, the representative value of the OCT data may be, for example, an average value of the plurality of OCT data, and addition average OCT data based on the plurality of OCT data is obtained. In a case where an average is used, the virtual image may also be reliably reduced by performing processing (for example, a trim average) of excluding an outlier and calculating an average. The representative value of the OCT data other than the average value may be, for example, a median value of the plurality of OCT data or a most frequent value of the plurality of OCT data.

For example, the image processor replaces data of the overlapping region of the real image and the virtual image in the OCT data with the other OCT data in which the real image and the virtual image overlap each other in a different region from the overlapping region as the complement processing, and thereby, the OCT data in which the data of the overlapping region is replaced with other OCT data may be generated. According to this, the data of the region where the real image and the virtual image overlap each other is replaced with good data in the other OCT data, and the highly reliable OCT data can be obtained even for the region where the real image and the virtual image overlap each other.

In a case where the complementary processing is performed, for example, the image processor may perform matching processing for correcting a positional shift between the plurality of OCT data obtained with different optical path lengths. Thereby, for example, the shift between the OCT data due to different optical path lengths can be corrected appropriately.

In a case where the complementary processing is performed, for example, the image processor may perform the complementary processing on a predetermined data region (including the zero delay position) with the zero delay position as a reference. Of course, the present invention is not limited to this, and the image processor may detect a data region including the overlapping region of the real image and the virtual image and may set the detected data region as the complementary region.

In a case where the complementary processing is performed based on the plurality of OCT data, for example, for at least one OCT data, both the front and rear OCT data may be used for the zero delay position, and the complementary processing may be performed on the overlapping region generated at the zero delay position and near the zero delay position. Accordingly, the entire OCT data can be used effectively, and a wide range of OCT data can be acquired smoothly.

<Virtual Image Excluding Processing>

Figure 8:
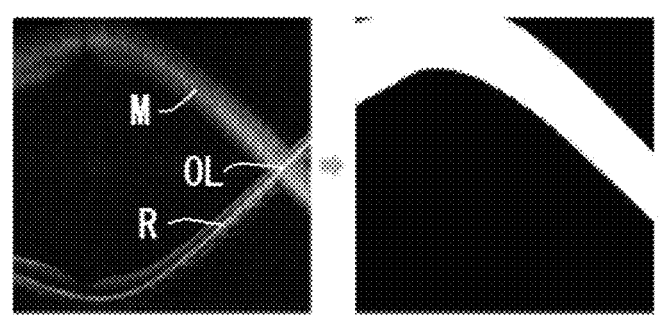
FIG. 8 is a diagram illustrating an example of a case where a virtual image region is removed prior to complementary processing.

The image processor may detect a virtual image region in the OCT data, and exclude the OCT data in the virtual image region to perform the complementary processing (see, for example, FIG. 8). According to this, for example, by excluding the virtual image, the OCT data from which the virtual image is appropriately excluded can be obtained. As the excluding processing, the OCT data corresponding to the virtual image may be reduced (suppressed), and it is not always necessary to exclude all of these.

As a method of excluding the OCT data of the virtual image region in the complementary processing, for example, the OCT data of the virtual image region may be removed in advance by image processing, or when the OCT data subjected to the complementary processing is obtained, the OCT data of the virtual image region may be excluded from the data, and the complementary processing may be performed on the OCT data in the real image region.

It is not always necessary to detect the virtual image region as a method of excluding the OCT data of the virtual image region. As described above, by obtaining representative value of the plurality of OCT data obtained with different optical path lengths, the OCT data in the virtual image region can be reduced as a result. This is because, in the OCT data obtained with the different optical path lengths, regions where the real image and the virtual image overlap each other are different from each other, and thus, by obtaining the representative value after the matching processing, an influence of the OCT data in the virtual image region is reduced as a result.

In the present embodiment, an example in which the virtual image region is detected and the complementary processing is performed with excluding the OCT data of the virtual image region is described, but the present invention is not limited to this, and the image processor can perform the complementary processing by detecting any one of the real image region and the virtual image region in the OCT data and excluding the OCT data of either one of the regions. That is, in an OCT apparatus, in a case where a real image and a virtual image are generated symmetrically by including an image quality for the zero delay position, it is not always necessary to exclude the virtual image, processing of removing the real image and leaving the virtual image may be performed, and the same effect can be obtained. Further, a method of removing the virtual image is not limited to the above-described method, and for example, a method described in JP-T-2015-506772 may be used.

The image processor may detect at least one of the real image region and the virtual image region in the OCT data based on the plurality of OCT data obtained with the different optical path lengths and exclude the OCT data of the real image region or the virtual image region based on the detection result to perform the complementary processing (see, for example, FIGS. 11 to 14). Thereby, for example, since the detection result of a region common to each other can be developed into each OCT data obtained with different optical path lengths, the excluding processing can be performed more accurately than when the real image region and the virtual image region are detected separately for each OCT data unit.

In this case, for example, a region which becomes an exclusion target may be detected, and the OCT data of the region may be excluded. Further, a region that becomes a remaining target may be detected, and the OCT data of the other region different from the OCT data of the region may be excluded. Further, these types of processing may be used together.

The image processor may include processing of matching at least one of the real image region and the virtual image region between the plurality of OCT data, during the processing of detecting at least one of the real image region and the virtual image region in OCT data based on the plurality of OCT data. Thus, for example, it is possible to detect smoothly at least one of the real image region and the virtual image region.

The image processor may generate a mask for excluding one of the real image region and the virtual image region from the OCT data, and the image processor may acquire the OCT data in which one of the real image region and the virtual image region is excluded by using the mask. Thereby, one of the real image region and the virtual image region can be accurately excluded. The mask may be generated based on the plurality of OCT data.

In a case where combined OCT data is generated based on the representative value of the plurality of OCT data obtained with different optical path length as the complementary process, the image processor may make a weighting coefficient different in a region to be excluded and a region to be left in the real image region and the virtual image region in the OCT data. For example, in a case where an addition average image of the plurality of OCT data is obtained, the weighting coefficient of the region to be left may increase and the weighting coefficient of the region to be excluded may be reduced. Thereby, one of the real image region and the virtual image region can be accurately excluded.

<Acquisition of Plurality of OCT Data Obtained with Different Optical Path Lengths>

Figure 7:
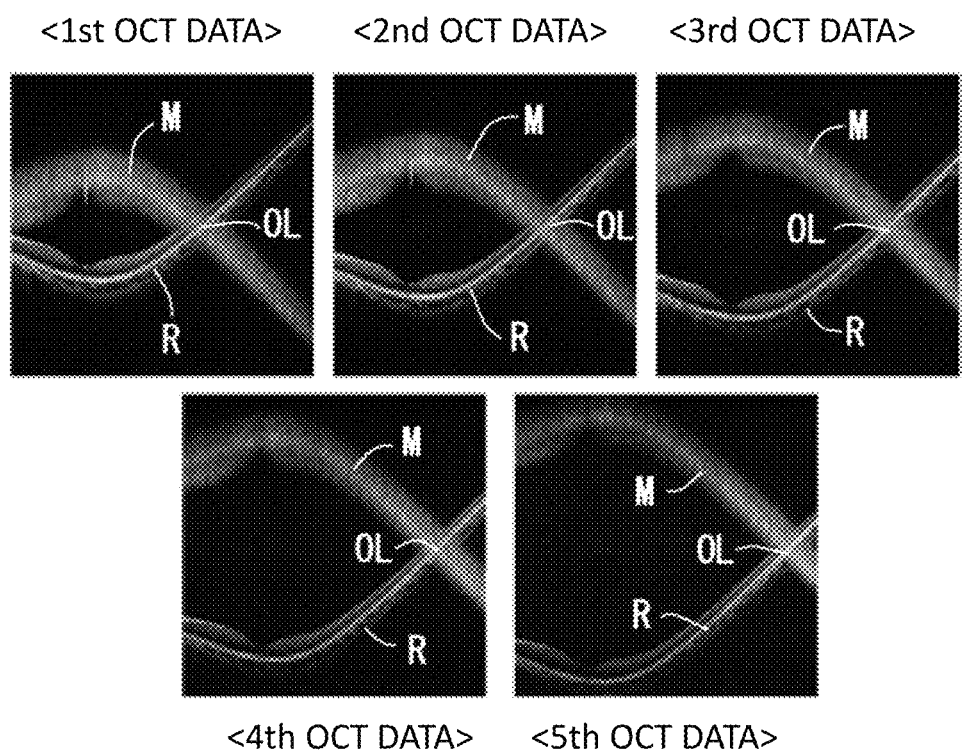
FIG. 7 is an example of a plurality of OCT data in the same part having different optical path lengths.

The plurality of OCT data obtained with different optical path lengths may be, for example, a plurality of OCT data obtained with different optical path lengths of at least one of a measurement light path and a reference light path when detecting a spectrum interference signal (see, for example, FIG. 7). In this case, the plurality of OCT data obtained with different optical path lengths differ in an optical path length difference of a predetermined part (for example, fundus) of a subject eye with respect to a zero delay position on each OCT data. Thus, the OCT data corresponding to the predetermined part of the subject eye differs in a relative position for the zero delay position with respect to a depth direction. The plurality of OCT data may be the OCT data of at least two frames. Each OCT data may be, for example, B-scan OCT data obtained by one-dimensional scanning (for example, line scanning) of measurement light, or may be three-dimensional OCT data obtained by two-dimensional scanning (for example, raster scanning) of the measurement light.

For example, an optical path length changing unit may be provided as a configuration for obtaining the plurality of OCT data obtained with different optical path lengths. The optical path length changing unit may be provided to change, for example, an optical path length of at least one of a measurement light path and a reference light path. The optical path length changing unit may change the optical path length by moving an optical member disposed in at least one of the measurement light path and the reference light path by a drive unit, and the optical path length may be changed by adjusting an operation distance between a subject eye and an apparatus.

The control unit may, for example, control the optical path length changing unit and sequentially acquire a spectrum interference signal serving as a basis for a plurality of OCT data obtained with different optical path lengths (see, for example, FIG. 8). Thereby, the plurality of OCT data for use in the complementary processing and the plurality of the OCT data obtained with different optical path lengths can be obtained smoothly with a simple configuration. The OCT data may be generated, for example, every time when each spectrum interference signal is acquired as timing at which the OCT data is generated, or after all spectrum interference signals are acquired, the OCT data corresponding to each spectrum interference signal may be generated, and the present invention is not limited in particular.

In this case, after acquiring the spectrum interference signal serving as a basis of a first OCT data with a first optical path length, the control unit may change the optical path length by controlling the optical path length changing unit, and acquire the spectrum interference signal serving as a basis of a second OCT data with a second optical path length. After acquiring the spectrum interference signal with the first optical path length, the control unit may automatically change the optical path length by automatically controlling the optical path length changing unit. Of course, the optical path length may be changed by a manual operation. In addition, the control unit may acquire the spectrum interference signal serving as a basis of a third OCT data with a third optical path length.

The image processor may perform the complementary processing on the overlapping region of the real image and the virtual image in the three-dimensional OCT data based on a plurality of the three-dimensional OCT data obtained with different optical path lengths. According to this, good three-dimensional OCT data is obtained in a region where the real image and the virtual image overlap each other. Thus, it is possible to acquire a wide range of good three-dimensional OCT data with a simple configuration.

In this case, for example, the control unit may control the optical path length changing unit to perform a first control for obtaining the spectrum interference signal serving as a basis of first three-dimensional OCT data with the first optical path length, and a second control for obtaining the spectrum interference signal serving as a basis of second three-dimensional OCT data with the second optical path length different from the first optical path length after the first control is performed.

The image processor may perform the complement processing on the overlapping portion between the real image and the virtual image in the three-dimensional OCT data, based on the first three-dimensional OCT data based on the spectrum interference signal obtained by the first control and on the second three-dimensional OCT data based on the spectrum interference signal obtained by the second control.

As an example of the first control and the second control, for example, the control unit may control the optical path length changing unit and the optical scanning unit, thereby, performing a first scanning control for scanning measurement light for each of a plurality of scanning lines with the first optical path length and a second scanning control for scanning the measurement light for each of the plurality of scanning lines with the second optical path length different from the first optical path length after the first scanning control is performed. According to this, while the optical path length is changed in units of each scanning line, the number of times of changing the optical path length is small, and a plurality of OCT data of each scanning line for use in the complementary processing can be obtained smoothly with a simple configuration. In this case, the complementary processing may be performed by using the OCT data of each scanning line corresponding to each other between the first scanning control and the second scanning control.

The scanning control is not limited to a case where the three-dimensional OCT data is obtained, and is effective, for example, in a case where the OCT data of a plurality of scanning lines having different scanning positions is acquired with a plurality of optical path lengths, and the complementary processing is performed on the OCT data of each scanning line. A scanning pattern of each scanning control includes, for example, a raster scan, a multi-scan in which a plurality of scanning lines separated from each other are scanned, a cross scan in which a plurality of scanning lines is scanned, and a radial scan in which a plurality of scanning lines are radially formed.

Positions of each scanning line between the first scanning control and the second scanning control may be the same. Thereby, it is possible to perform the complementary processing of the OCT data for each scanning line more accurately. Further, the positions of the scanning lines between the first scanning control and the second scanning control may be adjacent to each other. For example, in each scanning line (for example, 512 lines) corresponding to the raster scan, the scanning control relating to odd-numbered scanning lines may be performed in the first scanning control, and the scanning control relating to even-numbered scanning lines may be performed in the second scanning control. If the scanning lines are adjacent to each other, the complementary processing can be performed, and furthermore, imaging time can be shortened by reducing the number of scanning lines in one scanning control.

A scanning range relating to each OCT data may be performed in, for example, the same region. Of course, the present invention is not limited to this, and the scanning ranges may overlap in a range where the complementary processing can be performed and may be not necessarily the same. The complementary processing according to the present embodiment may be used, for example, in panoramic imaging of the OCT data.

<Application to Wide-Angle Fundus OCT Data>

In a case where a second imaging mode for obtaining OCT data on a wide-angle region including the fundus center area and the fundus peripheral area is set, the display control unit may output image regions in the front and rear direction of the zero delay position on the OCT data to the display unit and output the OCT data subjected to the complementary processing by the image processor to the display unit. According to this, it is possible to smoothly display a wide range of good OCT data.

An example of an embodiment of the OCT optical system for obtaining the OCT data of the wide-angle region will be described below. Of course, the OCT optical system according to the present embodiment is not limited to the following configuration.

<Angle-of-view Switching Optical System>

Hereinafter, a case where an angle-of-view switching optical system can be inserted into and removed from a light guiding optical system disposed on the measurement light path, and a size of an angle of view, which indicates a scanning range of the measurement light on the fundus is different between an insertion state and a retraction state will be described. In this case, in the embodiment, the size of the angle of view is more increased in the insertion state than in the retraction state. It is needless to say that the size is not limited thereto, and the size of the angle of view may be more decreased in the insertion state than in the retraction state.

The light guiding optical system is formed on the measurement light path. The light guiding optical system includes at least an optical scanning unit (optical scanner), and may further include an objective optical system. The optical scanner deflects the measurement light from the light splitter, and thereby the light guiding optical system forms a pivot point, at which the measurement light turns based on motion of the optical scanner, in an anterior portion of a subject eye and guides the measurement light passed through the pivot point to the fundus. Scanning of the measurement light about the pivot point on the fundus is performed in accordance with the motion of the optical scanner.

The objective optical system is an optical system that is disposed between the optical scanner of the light guiding optical system and the subject eye and is used for forming the pivot point. The pivot point is formed at a conjugated position of the optical scanner with respect to the objective optical system. The pivot point is also referred to as a "first pivot point". The objective optical system may be a refraction system including a lens, a reflection system including a mirror, or a combination of both of the systems.

The angle-of-view switching optical system is inserted into and removed from the light guiding optical system on the measurement light path. In this specification, a state in which the angle-of-view switching optical system is inserted into the light guiding optical system is referred to as an "insertion state", and a state in which the angle-of-view switching optical system is retracted from the light guiding optical system is referred to as a "retraction state". The size of the angle of view, which indicates a scanning range of the measurement light on the fundus, in the insertion state may be different from that in the retraction state. For convenience of description, unless otherwise noted, the angle-of-view switching optical system includes at least one lens in the following description.

Hereinafter, a state in which the angle of view is increased in the insertion state in which the angle-of-view switching optical system is inserted into the light guiding optical system is described. In this case, in the insertion state of the angle-of-view switching optical system, the angle of view is increased from the retraction state such that the measurement light is guided to the wide-angle region of the fundus.

The angle-of-view switching optical system may be inserted and may be removed from between the objective optical system included in the light guiding optical system and the subject eye. In this case, it is more preferable to have a lens disposition of a lens position of the angle-of-view switching optical system, in which a lens having principal power in the angle-of-view switching optical system is disposed to be inserted and removed from between the first pivot point and the subject eye. In the case of the disposition, it is easy to secure a longer operation distance than that in a case where the lens having the principal power is disposed between the objective optical system and the first pivot point.

In a case where the lens having the principal power in the angle-of-view switching optical system is inserted between the first pivot point and the subject eye, the angle-of-view switching optical system relays the first pivot point in the insertion state and forms a second pivot point. Specifically, the angle-of-view switching optical system forms the second pivot point by turning the measurement light passed through the first pivot point toward an optical axis in the insertion state. In the insertion state, the second pivot point is positioned in an anterior portion of the subject eye, and thereby scanning of the measurement light is performed on the fundus.

In this disclosure, a size of the scanning range of the measurement light on the fundus is described as an "angle of view". Here, the "angle of view" more depends on performance of an optical system that is disposed on the subject eye than the optical scanner and is a value obtained by assuming that the optical scanner is appropriately operated such that a maximum angle of view is realized.

<Compensation for Change in Light Path Length Difference>

When the angle-of-view switching optical system is inserted into and removed from the light guiding optical system, a light path length of the measurement light path is changed, and thus there can be found a light path length difference between the reference light and the measurement light. For example, since the angle-of-view switching optical system, which relays the pivot point formed by the objective optical system, is likely to be large in size and is likely to have a long light path length, the change in the light path length difference according to the insertion and the retraction is also considered to be increased. For example, there has been known a technology in which an attachment optical system is installed on an inspection window of fundus imaging OCT such that it is possible to image an anterior portion (for example, see "JP-A-2011-147612" or the like by the present applicant). In such an apparatus, a light path length of the measurement light path is changed before and after the attachment optical system is attached and detached. However, in the apparatus described above, the light path length of the attachment optical system is short, and an imaged site is switched to the anterior portion. In this manner, the light path length of the measurement light path in an ocular bulb is short, and thus a sufficient compensation length in the apparatus was about an ocular axial length ($\cong 32$ mm). By comparison, the light path length of the angle-of-view switching optical system in the embodiment is longer than the ocular axial length. For example, in the embodiment, it is necessary to compensate for an amount of change by about three to eight times an equivalent length to the ocular axial length in some cases. For example, in an example of design of the angle-of-view switching optical system that switches an angle of view from about 60° to about 100° in an OCT apparatus that is capable of performing imaging at the angle of view of about 60°, the light path length of the angle-of-view switching optical system was about 170 mm. In this manner, there is no configuration in the related art which is capable of coping with a change in the light path length of the measurement light path according to the insertion and the retraction of the angle-of-view switching optical system.

The OCT optical system may include a compensation unit that compensates for an amount of change in the light path length of the measurement light path between the insertion state and the retraction state.

The OCT optical system may include a plurality of reference light paths as the compensation unit. For example, the reference light path may branch to at least two paths of a first branched light path and a second branched light path. Here, the first branched light path has a first optical path length corresponding to a light path length of the measurement light path in the retraction state. In addition, the second branched light path has a second optical path length corresponding to a light path length of the measurement light path in the insertion state. A light path length difference between the first branched light path and the second branched light path may be determined in advance. Specifically, the light path length difference may be a length that is substantially equal to the light path length of the angle-of-view switching optical system.

The OCT optical system may cause the detector to simultaneously detect both of the interference signal due to the reference light from the first branched light path and an interference signal due to the reference light from the second branched light path or selectively detect any one of the two interference signals.

The reference lights from the light splitter are simultaneously guided to the first branched light path and the second branched light path, and thereby the interference signals due to the reference lights from both of the light paths of the first branched light path and the second branched light path can be simultaneously detected by the detector. However, in this case, a light path length difference between the measurement light and the reference light through the first branched light path and a light path length difference between the measurement light and the reference light through the second branched light path are replaced between "substantially 0" and "substantially a light path length of the angle-of-view switching optical system" based on the insertion and retraction of the angle-of-view switching optical system. Therefore, strength of one interference signal corresponding to a state (insertion state/retraction state) of the light guiding optical system of the two types of interference signals having a different path of the reference light path from each other is obviously stronger than that of the remaining one. In a case where the light path length of the angle-of-view switching optical system is sufficiently long, the interference signal of the remaining one has a level of strength which does not cause a problem. In the retraction state, the interference signal by the reference light through the first branched light path is a signal having a signal strength that is stronger than that of the interference signal by the reference light through the second branched light path, and vice versa in the insertion state. The light from the OCT light source is split to the measurement light and the reference light by the light splitter; however, it is not essential for a side of the reference light path to have an element such as the subject eye, which significantly attenuates a beam. Therefore, even when the first branched light path and the second branched light path which branch from the reference light path are formed, sufficient intensity is secured to obtain the interference signal on both of the branched light paths. Therefore, even in a configuration in which either light path length of the measurement light path or the reference light path is switched according to the insertion and the retraction of the angle-of-view switching optical system, it is possible to perform good acquisition of the OCT data based on the interference signal detected by the detector.

The OCT optical system may have, as a part of the compensation unit, a switch (an example of a drive unit) that switches the light path, through which the reference light is guided from the light splitter, between the first branched light path and the second branched light path. Consequently, the detector can selectively detect one of the interference signal by the reference light from the first branched light path and the interference signal by the reference light from the second branched light path. For example, a controller of the OCT apparatus may cause the switch to perform switching depending on the state (insertion state/retraction state) of the light guiding optical system. In other words, the switch may be controlled to be driven such that the reference light from the light splitter is guided to the first branched light path in the retraction state, and the reference light from the light splitter is guided to the second branched light path in the insertion state. A method of compensating for an amount of change in the light path length on the measurement light path is considered to be particularly advantageous in a case where the light path length of the angle-of-view switching optical system is relatively short or the like, compared with a system without the switch.

In addition, the reference light path branching as described above is not absolutely necessary to be provided. In this case, the compensation unit may adjust at least one length of the measurement light path and the reference light path, for example. For example, in a case where the compensation unit adjusts the light path length of the reference light path, the compensation unit may switch the light path length of the reference light path, to which the reference light is guided from the light splitter, between the first optical path length corresponding to the light path length of the measurement light path in the retraction state and the second optical path length corresponding to the light path length of the measurement light path in the insertion state. In addition, in a case where the compensation unit adjusts the light path length of the measurement light path, the compensation unit may change a light path length between the light splitter and the optical scanner on the measurement light path, thereby compensating for an amount of change in the light path length according to the insertion and the retraction of the angle-of-view switching optical system described above.

<Dispersion Correction>

In addition, the OCT apparatus of the embodiment includes a dispersion correcting unit (dispersion compensating unit) that corrects (compensates for) a dispersion amount in an optical system between the measurement light path and the reference light path, thereby being capable of obtaining good OCT data. The dispersion correcting unit may correct the dispersion amount optically or may correct in a signal processing manner (including at least one of signal processing or calculation). In a case of the former, the dispersion correcting unit is an element of the OCT optical system. In a case of the latter, the dispersion correcting unit is an electronic circuit (may be a dedicated circuit or an image processor) which is connected to the detector.

Incidentally, in the embodiment, the angle-of-view switching optical system is inserted into or removed from the light guiding optical system, and thereby the dispersion amount in the optical system between the measurement light path and the reference light path is likely to be changed. In the OCT apparatus of the embodiment, a plurality of different correction values of the dispersion amount may be set in the dispersion correcting unit. At least a first correction value for correcting a dispersion amount in the retraction state and a second correction value for correcting the dispersion amount in the insertion state are set, and thereby it is possible to acquire good OCT data in both cases where the angle-of-view switching optical system is inserted and removed.

In addition, the correction value of the dispersion correcting unit may be further subdivided. For example, since the dispersion amount in the optical system between the measurement light path and the reference light path can vary for each scanning angle of the optical scanner, the first correction value, the second correction value, or both correction values may be set as different values for each scanning angle of the optical scanner. In particular, in a case where a scanning range is performed at a wide angle in the insertion state of the angle-of-view switching optical system, a case of having a significant difference between a dispersion amount related to measurement light, with which the fundus center area is irradiated, and a dispersion amount related to measurement light, with which the fundus peripheral area is irradiated, is considered. In the OCT apparatus of the embodiment, a different correction value may be set for each of at least the fundus center area and the fundus peripheral area.

<Light-Flux Diameter Changer>

In addition, in the OCT apparatus of the embodiment, the angle-of-view switching optical system is inserted into the light guiding optical system, and thereby a light-flux diameter of the measurement light is considered to be increased. In this case, a spot size of the measurement light on the fundus increases as a light-flux diameter increases in the insertion state, and thereby image resolving power is considered to be more degraded, compared with the retraction state. In this respect, the OCT apparatus of the embodiment includes a light-flux diameter changer. Here, the light-flux diameter changer adjusts a light-flux diameter of the measurement light with which the subject eye is irradiated. The controller (processor) of the OCT apparatus causes the light-flux diameter changer to switch the light-flux diameter in association with a state (insertion state/retraction state) of the light guiding optical system, and thereby it is possible to change the image resolving power before and after the angle-of-view switching optical system is inserted and removed. More specifically, in a case where the state is switched from the retraction state to the insertion state, the controller drives the light-flux diameter changer such that the light-flux diameter of the measurement light decreases. In addition, in a case where the state is switched from the insertion state to the retraction state, the light-flux diameter changer is driven such that the light-flux diameter of the measurement light increases. Consequently, the change in spot size of the measurement light is corrected. Since the spot size is substantially proportional to an angle of view, it is preferable to drive the light-flux diameter changer by a correction amount in association with a ratio of the angle of view (scanning range) between the insertion state and the retraction state.

EXAMPLE

Hereinafter, an optical coherence tomography (OCT) apparatus shown in FIGS. 1 and 2 will be described as an example. For example, the OCT apparatus according to the example has spectral domain OCT (SD-OCT) as a basic configuration.

Figure 2:
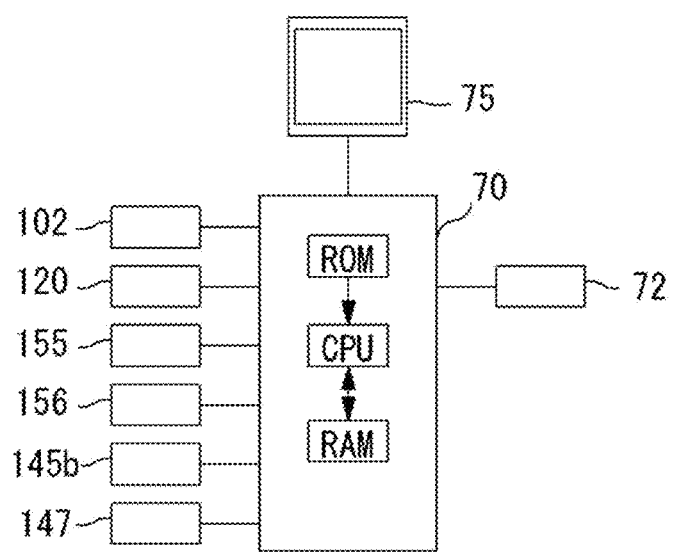
FIG. 2 is a diagram illustrating an example of a control system of the OCT apparatus according to the present embodiment.

An OCT apparatus 1 includes a light source 102, an interference optical system (OCT optical system) 100, and a calculation controller (calculation control unit) 70 (refer to FIG. 2). Additionally, in the OCT apparatus, a memory 72, a display unit 75, a front image observing system and a fixation target projecting system (not shown) may further be provided. The calculation controller (hereinafter, a processor) 70 is connected to the light source 102, the interference optical system 100, the memory 72, and the display unit 75.

The interference optical system 100 guides the measurement light to an eye E by a light guiding optical system 150. The interference optical system 100 guides the reference light to a reference optical system 110. The interference optical system 100 causes a detector (light receiving element) 120 to receive an interference signal light that is acquired due to interference of the reference light with the measurement light reflected from the eye E. The interference optical system 100 is mounted in a housing (apparatus main body) (not shown), and the housing moves three-dimensionally with respect to the eye E by a known alignment moving mechanism via an operation unit such as a joystick. In this manner, alignment may be performed with respect to the subject eye.

The SD-OCT type may be used for the interference optical system 100. A light source that emits a light-flux having a short coherence length is used as the light source 102, and a spectroscopic detector that performs spectroscopic dispersion and detects a spectral interference signal for each wavelength component is used as the detector 120.

A coupler (splitter) 104 is used as a first light splitter and splits the light emitted from the light source 102 to light traveling to the measurement light path and light traveling to the reference light path. For example, the coupler (fiber coupler) 104 guides the light from the light source 102 to an optical fiber 152 on a side of the measurement light path and guides the light to a coupler (fiber coupler) 140 on a side of the reference light path via a fiber 106. Consequently, the light from the light source 102 is guided to the reference optical system 110.

<Light Guiding Optical System>

The light guiding optical system 150 is provided to guide the measurement light to the eye E. For example, in the light guiding optical system 150, the optical fiber 152, a collimator lens 154, a variable beam expander 155, an optical scanner 156, and an objective lens system 158 (the objective optical system in the example) are provided in this order. In this case, the measurement light is emitted from an emission end of the optical fiber 152 and becomes a parallel beam by the collimator lens 154. Then, the light travels toward the optical scanner 156 in a state of having a desired light-flux diameter by the variable beam expander 155. The eye E is irradiated with the beam passing through the optical scanner 156 via the objective lens system 158. A first pivot point P1 is formed at a conjugated position of the optical scanner 156 with respect to the objective lens system 158. The anterior portion is positioned at the pivot point P1, and thereby the measurement light reaches the fundus without eclipse. In addition, the fundus is scanned with the measurement light depending on the operation of the optical scanner 156. In this case, the measurement light is scattered-reflected by tissue of the fundus.

The optical scanner 156 may scan the eye E with the measurement light in XY directions (transverse directions). For example, the optical scanner 156 is configured of two galvano mirrors, and a reflection angle of the mirror is adjusted optionally by a driving mechanism. A reflection (traveling) direction of the light-flux emitted from the light source 102 changes, and the fundus is scanned in any optional direction. For example, as the optical scanner 156, an acousto-optic modulator (AOM) or the like that changes the traveling (deflection) direction of light may be used, in addition to a reflective mirror (a galvano mirror, a polygon mirror, or a resonant scanner).

Scattered light (reflected light) of the measurement light from the eye E travels back via a path used during light projection, is incident to the optical fiber 152, and reaches the coupler 104. The coupler 104 guides the light from the optical fiber 152 to a light path toward the detector 120.

<Attachment Optical System>

An attachment optical system 160 (an example of the "angle-of-view switching optical system") in the OCT apparatus according to the example is inserted and removed from between the objective optical system 158 in the light guiding optical system 150 and the subject eye E. A lens tube including the attachment optical system is attached to and detached from a housing surface (not shown), and thereby the attachment optical system 160 is inserted and removed from between the objective optical system 158 and the subject eye E.

The attachment optical system 160 may include a plurality of lenses 161 to 164. Here, a lens having principal power in the attachment optical system 160 shown in FIG. 1 is the lens 164 placed in front of the subject eye. An insertion/retraction position of at least the lens 164 is between the first pivot point P that is formed by the objective optical system 158 and the subject eye E. At least the lens 164 turns the measurement light passed through the first pivot point P1 toward an optical axis L, and thereby a second pivot point P2 is formed at a conjugated position of the optical scanner 156 with regard to the attachment optical system 160 the objective optical system 158. In other words, the attachment optical system 160 is an optical system that relays the pivot point P1 to the pivot point P2.

In the example, a solid angle of the measurement light at the second pivot point P2 is larger than a solid angle at the first pivot point P1. For example, the solid angle at the second pivot point P2 is increased as twice or more as the solid angle at the first pivot point P1. In the example, it is possible to perform scanning at an angle of view of about 60° in the retraction state, and it is possible to perform scanning at an angle of view of about 100° in the insertion state.

The variable beam expander 155 is the light-flux diameter adjusting unit in the example. As an example, the variable beam expander 155 may include a plurality of lenses that form a both-side telecentric optical system and may be configured to switch a light-flux diameter by changing a lens space by an actuator. The variable beam expander 155 adjusts the light-flux diameter of the measurement light based on an instruction from the controller 70.

If the light-flux diameter of the measurement light that is guided from the variable beam expander 155 to the optical scanner 156 is constant between the insertion state and the retraction state, the spot size of the measurement light is proportional to the angle of view on the fundus. Therefore, the resolving power is more degraded in the insertion state than in the retraction state. In the example, the controller 70 drives the variable beam expander 155 according to the insertion and the retraction of the attachment optical system and more decreases the light-flux diameter in the insertion state than in the retraction state. A rate of the light-flux diameters (light-flux diameters in the variable beam expander 155) in the insertion state and the retraction state is inversely proportional to the angle of view in the insertion state and the retraction state, and thereby it is possible to suppress a change in resolving power based on the insertion and retraction of the attachment optical system 160.

Incidentally, in order to secure a sufficient operation distance, the attachment optical system 160 needs to cause the measurement light to be tuned from a position having a sufficient light beam height toward the optical axis L. In addition, in order to suppress an aberration caused by the attachment optical system 160 within a permissible range, power of the lenses included in the attachment optical system 160 is limited. Hence, it is difficult to shorten the light path length of the attachment optical system 160.

Although there is an OCT apparatus in the related art that is configured to adjust the light path length difference between the reference light and the measurement light, there is no OCT apparatus that has an adjustment range that is applicable to the insertion and retraction of the attachment optical system 160. For example, in the related art, there has been known a technology in which an optical adapter is installed such that it is possible to perform imaging an anterior portion in fundus imaging OCT (for example, see "JP-A-2011-147612" or the like by the present applicant). However, the optical adapter does not relay the pivot point formed by an optical system of an apparatus main body, and there is no demand for a wide-angle scanning range. Therefore, the optical adapter can be formed to have a relatively short light path length. Further, a position of an image surface is changed from the fundus to the anterior portion in response to insertion of the optical adapter. Hence, there is no need to significantly adjust the light path length difference in response to the insertion of the optical adapter.

<Reference Optical System>

The reference optical system 110 generates the reference light that is combined with fundus reflection light of the measurement light. The reference light passing through the reference optical system 110 is coupled and interferes with light from the measurement light path by a coupler (Fiber coupler) 148. The reference optical system 110 may be one of a Michelson type or a Mach-Zehnder type.

The reference optical system 110 shown in FIG. 1 is formed by a transmission optical system. In this case, the reference optical system 110 does not cause the light from the coupler 104 to return but transmits the light, thereby guiding the light to the detector 120. The reference optical system 110 is not limited thereto and may be formed by a reflection optical system and guide the light from the coupler 104 to the detector 120 by causing the light to be reflected from the reflection optical system, for example.

In the example, the reference optical system 110 may have a plurality of reference light paths. For example, in FIG. 1, the coupler (fiber coupler) 140 causes the reference light path to branch to a light path (the first branched light path in the example) via which a fiber 141 passes and a light path (the second branched light path in the example) via which a fiber 142 passes. The fiber 141 and the fiber 142 are connected to a coupler (fiber coupler) 143. Consequently, two branched light paths are coupled, and light is incident to the coupler 148 via a light path length difference adjusting unit 145 and a polarization controller 147.

In the example, the reference light from the coupler 104 is simultaneously guided to the fiber 141 and the fiber 142 by the coupler 143. Light passing through either the fiber 141 or the fiber 142 is coupled with the measurement light (fundus reflection light) in the coupler 148.

A light path length difference between the fiber 141 and the fiber 142, that is, a light path length difference between the first branched light path and the second branched light path, may be a fixed value. In the example, the light path length difference is set to be substantially equal to the light path length of the attachment optical system 160.

An optical member for adjusting the light path length difference between the measurement light and the reference light may be disposed on at least any one of the measurement light path and the reference light path. As an example, the reference light path adjusting unit 145 is provided in the optical system shown in FIG. 1, and a mirror 145*a* having two orthogonal surfaces is provided at a corresponding position so as to control the light path length difference between the measurement light and the reference light. The mirror 145*a* moves in an arrow direction by an actuator 145*b*, and thereby it is possible to increase and decrease the light path length of the reference light path. It is needless to say that a configuration, in which the light path length difference between the measurement light and the reference light is adjusted, is not limited thereto. For example, in the light guiding optical system 150, the collimator lens 154 and a coupler 153 move integrally, and thereby the light path length of the measurement light is adjusted. As a result, the light path length difference between the measurement light and the reference light may be adjusted.

Here, In the example, since the reference light path adjusting unit 145 is provided on a light path between the coupler 143 and the coupler 148, that is, on a common light path between the first branched light path and the second branched light path, it is possible to perform adjustment of an ocular axial length with regard to an individual difference, which is the adjustment of the light path length difference between the measurement light path and the reference light path, with respect to both of the first branched light path and the second branched light path.

It is preferable that an adjustment range of the light path length in the reference light path adjusting unit 145 is set to be sufficiently shorter than the light path length difference between the fiber 141 and the fiber 142 (in other words, the light path length difference between the first branched light path and the second branched light path).

<Correction of Manufacturing Tolerance of Zero-Delay Position>

Incidentally, a zero-delay position (a position at which the light path length difference between the measurement light path and the reference light path is zero) is considered to be different for each device of the attachment optical system 160 due to a manufacturing tolerance of the attachment optical system 160 and the fiber 142. For example, the manufacturing tolerance can be corrected by adjusting an initial distance value of a distance between the collimating lens 154 and a diopter correcting lens in the light guiding optical system 150. The OCT apparatus 1 may include an adjusting mechanism (not shown) for adjusting such a manufacturing error. The adjusting mechanism may be configured to be capable of performing adjustment after a product delivery of the OCT apparatus 1.

<Light Detector>

The detector 120 is provided to detect interference of the light from the measurement light path with the light from the reference light path. In the example, the detector 120 is a spectroscopic detector and includes an optical spectrometer and a line sensor, for example, in which the measurement light and the reference light which are coupled by the coupler 148 are scattered by the optical spectrometer and are received in a different region (pixel) of the line sensor for each wavelength. Consequently, an output for each pixel is acquired as a spectral interference signal.

Since a curvature of the fundus does not necessarily match an image forming surface of the measurement light, and a displacement between both of a fundus center area and a fundus peripheral area increases in at least one of the areas in the insertion state of the attachment optical system 150, it is preferable to secure a sufficient depth range in the light detector in consideration of the displacement. For example, in the SD-OCT, it is preferable to provide a line camera having a sufficient number of pixels with respect to an anticipated depth range. In addition, the following configuration may be further employed as "modification examples".

<Acquisition of Depth Information>

The controller 70 performs processing (Fourier analysis) on a spectral signal detected by the detector 120 and obtains OCT data of the subject eye.

The spectral signal (spectral data) may be rewritten as a function of a wavelength $\lambda$ and may be converted to an equal interval function I (k) with regard to a wave number k ($=2\pi/\lambda$)). Alternatively, the spectral signal may be acquired as an equal interval function I (k) with regard to the wave number k from the beginning (a k-clock technology). The calculation controller may perform Fourier transform of the spectral signal in a space having the wave number k, thereby obtaining OCT data in a depth (Z) region.

Further, information after the Fourier transform may be obtained as a signal containing a real component and an imaginary component in a Z space. The controller 70 may obtain absolute values of the real component and the imaginary component in the signal in the Z space, thereby acquiring the OCT data.

Here, in the coupler 148, the reference light passing through the first branched light path and the reference light passing through the second branched light path are simultaneously guided and each is coupled to the measurement light. Since a large light path length difference, which is substantially equal to the light path length of the attachment optical system 160, occurs between the first branched light path and the second branched light path, one of the reference light passing through the first branched light path and the reference light passing through the second branched light path is likely to interfere with the measurement light; however, the other reference light is unlikely to interfere with the measurement light. Although the spectral interference signal from the detector 120 contains a component due to the reference light passing through the first branched light path and a component due to the reference light passing through the second branched light path, one of the two types of components according to the state of the light guiding optical system 150 is obtained as a remarkably stronger signal than the other. As a result, it is possible to obtain good OCT data regardless of the state of the light guiding optical system 150. In other words, the OCT apparatus according to the example has the light path length difference corresponding to the attachment optical system 160 and includes the plurality of reference light paths, and thereby the amount of change according to the insertion and the retraction of the attachment optical system 160, which is the amount of change in the light path length difference on the measurement light path, is compensated regardless of the state of the light guiding optical system 150.

The reference light path adjusting unit 145 needs to be controlled to adjust the light path length difference related to the ocular axial length of the subject eye E, which is the light path length difference between the measurement light path and the reference light path, in advance. For example, in the example, the mirror 145*a* may be moved in a predetermined adjustment range, an interference signal may be acquired at each position, and the position of the mirror 145*a* may be determined on the basis of a position, at which the strength of the interference signal has the highest strength. In a case where the adjustment range of the light path length in the reference light path adjusting unit 145 is sufficiently small with respect to the light path length difference between the first branched light path and the second branched light path, at a position in the adjustment range of the reference light path adjusting unit 145, at which the interference signal has a strength peak, can be uniquely identified.

Since the fundus reflection light of the measurement light from the fundus peripheral area is weaker than the reflected light from the fundus center area in the insertion state, the light path length difference between the measurement light path and the reference light path may be adjusted by the reference light path adjusting unit 145 such that the zero-delay position between the measurement light path and the reference light path overlaps anticipated fundus tissue (for example, the retina, the choroid, the sclera, or the like) in the fundus peripheral area.

<Dispersion Correction by Software>

In the present embodiment, a controller 70 may perform the dispersion correction processing on the spectrum data output from the detector 120 using software. The controller 70 obtains the OCT data based on the spectrum data after the dispersion correction. Therefore, there occurs a difference in image quality between the real image and the virtual image.

That is, in the present embodiment, a difference in the amount of dispersion of the optical system between a measurement light path and a reference light path is corrected by signal processing. Specifically, the correction value stored in advance in the memory 72 is applied in the spectrum signal processing.

The controller 70 acquires a spectrum intensity of the light based on the received light signal output from the detector 120 and rewrites the spectrum intensity as a function of the wavelength $\lambda$. Next, the spectrum intensity I ($\lambda$) is converted into a function I (k) that is evenly spaced with respect to the wave number k ($=2\pi/\lambda$).

The influence of the dispersion mismatch between the measurement light and the reference light shifts the phase of the interference component, decreases the peak of the multiplexed signal of each wavelength, and spreads the signal (decreases the resolution). Therefore, in the dispersion correction, by returning the phase shifted for each wavelength, the decrease in the resolution due to the decrease in the interference signal is corrected. In this case, the phase shift amount $\phi$ (k) as a function of the wave number k is obtained, and the phase shift is returned for each value of k by "I (k)×exp−i$\phi$ (k)". Here, the phase $\phi$ (k) to be subjected to the dispersion correction can be obtained in advance by calibration, or the phase $\phi$ (k) corresponding to the acquired tomographic image may be obtained. Then, a parameter for dispersion correction (for example, a phase $\phi$ (k)) is stored in the memory 72.

Thereafter, the controller 70 obtains the OCT data by performing the Fourier transform on the spectrum intensity I (k) after the dispersion correction which is a result of correction by the set dispersion correction data.

For example, a first dispersion correction value (for normal image) is acquired from the memory 72 as a dispersion correction value for correcting the influence of the dispersion on the real image, the spectrum data output from the detector 120 is corrected using the first dispersion correction value, and the Fourier transform is performed on the corrected spectral intensity data to form the OCT data. The real image R is acquired as a high sensitivity and high resolution image, and the virtual image M (the mirror image) is acquired as a low resolution blurred image due to the difference in dispersion correction value.

In this way, when a real image is acquired in a first image area G1, the real image is acquired as a high sensitivity and high resolution image, and the virtual image (the mirror image) is acquired in a second image area G2 as a low resolution blurred image due to the difference in dispersion correction value. On the other hand, when a real image is acquired in the second image area G2, the virtual image is acquired in the first imaging area G1 as a low resolution blurred image due to the difference in dispersion correction value.

Of course, not limited to the description above, the software dispersion correction may be performed on the virtual image M. In this case, the virtual image M is acquired as a high sensitivity and high resolution image, and the real image R is acquired as a low resolution blurred image.

For details of the method of performing the dispersion correction by the software described above, U.S. Pat. No. 6,980,299 and JP-T-2008-501118, and the like may be referred to. In addition, JP-A-2010-29648 may be referred to.

In a case where the dispersion correction processing by the software is performed, when obtaining the OCT data on the fundus center area, for example, the controller 70 may extract the image data having the higher sensitivity and resolution among the image data of the real image and the virtual image.

In the example, a first correction value corresponding to the retraction state and a second correction value which is a value different from the first correction value and corresponds to the insertion state are stored in a memory 72 in advance, and a correction value to be applied is switched according to the state of the light guiding optical system 150. As a result, in the OCT apparatus according to the example, an amount of change according to the insertion and retraction of the attachment optical system 160, which is an amount of change in the dispersion amount between the measurement light path and the reference light path, is compensated in each state of the light guiding optical system 150.

Further, in the example, a plurality of second correction values corresponding to the insertion state are set depending on scanning positions of the measurement light. Specifically, a correction value for the fundus center area and a correction value for the fundus peripheral area are set as second correction values which are different from each other. For example, the first correction value may be applied to a region within an angle of 60° of the fundus, and the second correction value may be set as a value that is applied to a region apart from the region at the angle of 60°. Since the attachment optical system 160 has significant power, overall, a significant difference in dispersion amount is considered to occur between a light-flux passing through the fundus center area and a light-flux passing through the fundus peripheral area. By comparison, in the example, since the correction value of the dispersion amount changes depending on an irradiation position of the fundus with the measurement light, it is possible to obtain good OCT data in the wide-angle region of the fundus.

It is needless to say that the second correction value may be further subdivided. For example, the entire fundus is divided into the fundus center area, a first fundus peripheral area on an outer side from the fundus center area, and a second fundus peripheral area on an outer side from the first fundus peripheral area, and a correction value corresponding to the fundus center area, a correction value corresponding to the first fundus peripheral area, and a correction value corresponding to the second fundus peripheral area may be set to be different from each other as the second correction value.

<Control System>

The controller 70 may include a CPU (processor), a RAM, a ROM, and the like (refer to FIG. 2). For example, the CPU of the controller 70 may control the OCT apparatus. The RAM stores various types of information temporarily. For example, in the ROM of the controller 70, various programs for controlling operations of the OCT apparatus, the initial value, or the like may be stored.

The non-volatile memory (hereinafter, simply abbreviated to "memory") 72 as the storage unit, the display unit 75, and the like are electrically connected to the controller 70. A non-transitory storage medium, which is capable of storing the storage content even when an electric power supply is cut off, may be used for the memory 72. For example, a hard disk drive, a flash ROM, a USB memory that is removably installed in the OCT apparatus or the like can be used as the memory 72. The memory 72 may store a control program for controlling the acquisition of the OCT data and the imaging of an OCT image. In addition, the memory 72 may store various types of information related to imaging other than the OCT image generated from the OCT data. The display unit 75 may display the OCT image generated from the OCT data.

An insertion/retraction detector that automatically detects whether or not the attachment optical system 160 is inserted into the light guiding optical system may be provided, and the controller may perform control or processing of each member of the OCT optical system 100 based on a detection signal from the detector. For example, switching control of the light-flux diameter by the variable beam expander 155, setting control of the zero-delay position by the reference light path adjusting unit 145, change processing of the dispersion amount in the optical system between the measurement light path and the reference light path, or the like may be appropriately performed as described above. The insertion detector may be a sensor disposed in the vicinity of the objective optical system 158.

It is needless to say that an examiner may input information that identifies the state of the light guiding optical system (the insertion state/retraction state of the attachment optical system) on a user interface (UI) of the OCT apparatus, and thereby the controller may perform the control and the processing of each member in the OCT optical system 100 based on the corresponding information.

<Imaging Mode Setting>

In the OCT apparatus according to the present embodiment, the first imaging mode for obtaining the OCT data on the fundus center area and the second imaging mode for obtaining the OCT data on the wide-angle region including the fundus center area and the fundus peripheral area may be settable. In this case, for example, in the first imaging mode, the scanning range of the measurement light on the fundus may be set on the fundus center area, and in the second imaging mode, the scanning range of the measurement light onto the fundus may be set on the wide-angle region including the fundus center area and the fundus peripheral area.

In this case, for example, the controller 70 may switch the imaging mode between the first imaging mode and the second imaging mode based on an operation signal from an operation unit operated by the examiner. In addition, the controller 70 may automatically switch the imaging mode between the first imaging mode and the second imaging mode. In addition, the controller 70 may perform a guide display prompting the switching of the imaging mode between the first imaging mode and the second imaging mode.

The controller 70 may automatically switch the imaging mode between the first imaging mode and the second imaging mode based on a detection signal from an insertion and retraction detection unit (may perform the guide display). If the scanning range of the measurement light is within the predetermined range, the controller 70 may set the imaging mode as the first imaging mode, and if the scanning range of the measurement light exceeds the predetermined range, then, may set the imaging mode as the second imaging mode. The mode switching may be performed automatically or via the guide display.

After automatically adjusting a difference in optical path length between the measurement light and the reference light, if the real image R of the OCT data in the first image area G1 is on the zero delay (or if the real image R of the OCT data is detected in the second image area G2 also), the controller 70 may automatically switch the imaging mode to the second imaging mode or may perform the guide display. If the difference in optical path length is automatically adjusted, an adjustment may be performed such that a retinal portion in the OCT data of the fundus center area is formed in the first image area G1.

<Switching of Display State of OCT Data according to Imaging Mode>

The controller 70 may switch the display state of the OCT data on the display unit 75 between the first imaging mode and the second imaging mode (for example, refer to FIGS. 3A, 3B, 4A and 4B). In this case, for example, the controller 70 may change the output range of the OCT data on a display screen of the display unit 75 according to the imaging mode. If the imaging mode is set as the first imaging mode, the controller 70 may set the output range of the OCT data in the depth direction as a first output range, and if the imaging mode is set as the second imaging mode, the controller 70 may set the output range of the OCT data in the depth direction as a second output range which is wider than the first output range. In this case, in the second the output range, the output range may be set such that OCT data of an area from the fundus center area to the fundus peripheral area is output to the display screen of the display unit 75.

The controller 70 may change the display magnification of the OCT data on the display screen of the display unit 75 according to the imaging mode. In this case, the controller 70 may change the vertical magnification, or may change at least one of the vertical magnification and the horizontal magnification. In addition, the controller 70 may change the display range of the OCT data on the display screen of the display unit 75. In this case, the controller 70 may change the display range in the vertical direction, or may change the display range in at least one of the vertical direction and the horizontal direction.

Figure 3A:
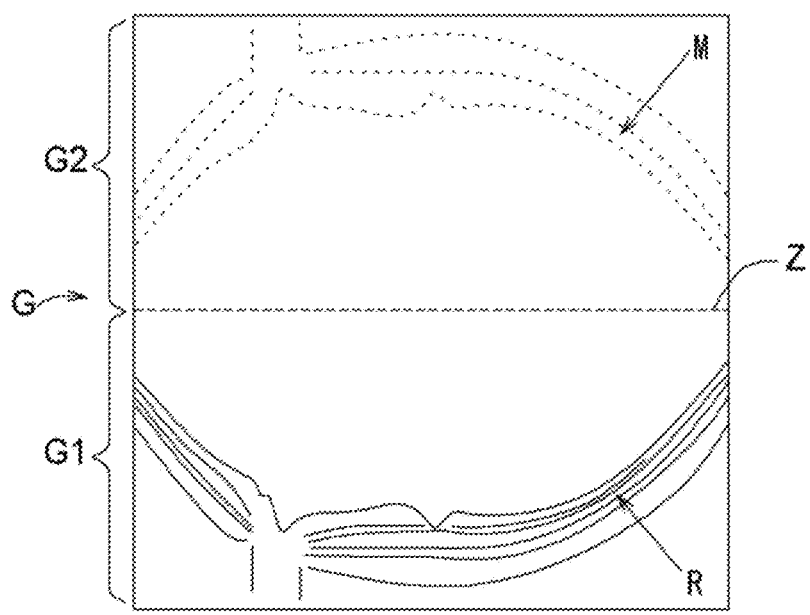
FIG. 3A is a diagram illustrating an example of OCT data obtained during a normal imaging according to the present embodiment.
Figure 3B:
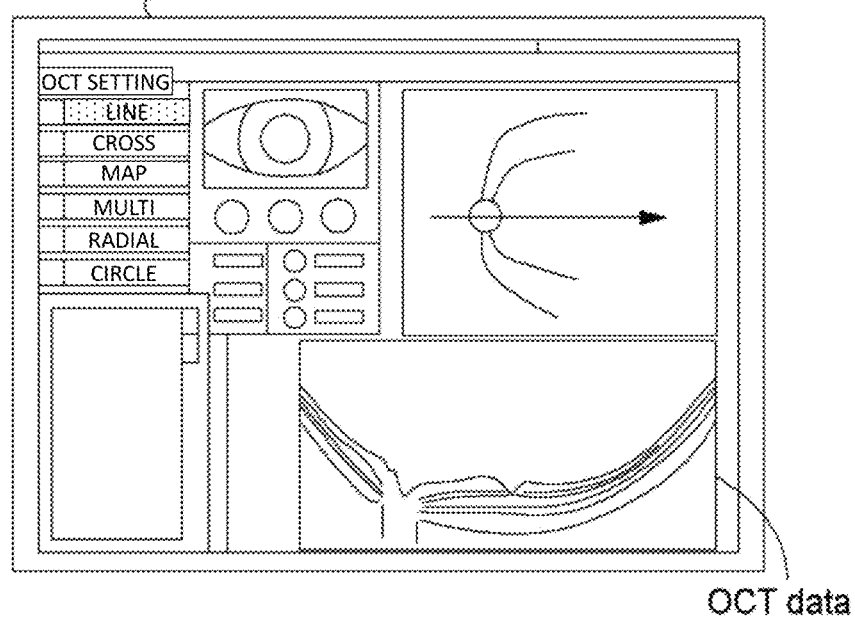
FIG. 3B is a diagram illustrating an output example on a display unit during the normal imaging.
Figure 4A:
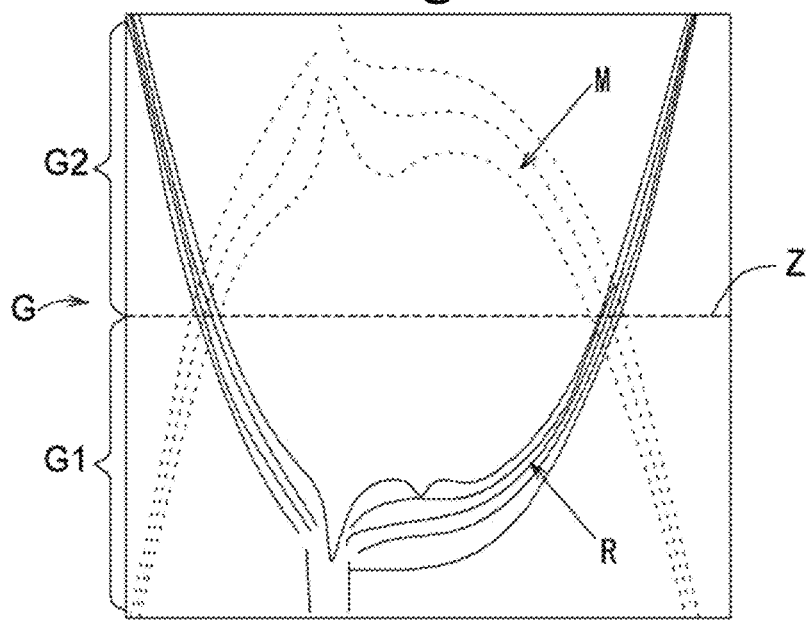
FIG. 4A is a diagram illustrating an example of OCT data obtained during a wide-angle imaging according to the present embodiment.
Figure 4B:
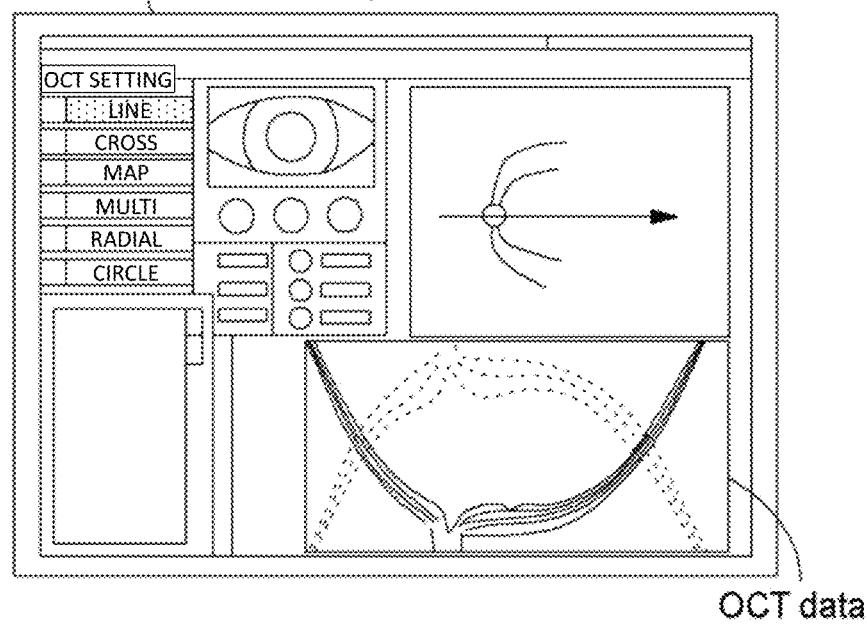
FIG. 4B is a diagram illustrating an output example on the display unit during the wide-angle imaging.

FIGS. 3A and 4A are diagrams illustrating examples of the OCT data acquired by the OCT optical system 100, and FIGS. 3B and 4B are diagrams illustrating examples of the output on the display unit. A zero delay position Z is a position of the reference light in the OCT data corresponding to an optical path length and corresponds to a position where the optical path length of the measurement light and the reference light match each other. The OCT data is formed of a first imaging area G1 corresponding to the inner side of the zero delay position Z and the second imaging area G2 corresponding to the front side of the zero delay position Z. For example, the first imaging area G1 and the second imaging area G2 have a symmetrical relation with respect to the zero delay position Z.

FIG. 3A is a diagram illustrating an example of OCT data obtained in the first imaging mode, and FIG. 3B is a diagram illustrating an example of an output of the OCT data obtained in the first imaging mode on the display unit.

For example, the controller 70 may adjust the difference in optical path length between the measurement light and the reference light such that the retinal surface in the fundus center area is formed at the inner side of the zero delay position Z or such that the rear side of a choroid in the fundus center area is formed at the front side of the zero delay position Z.

When the retinal surface in the fundus center area is formed at the inner side of the zero delay position Z (retinal mode), each of the tomographic images formed in the first imaging area and in the second imaging area is in a state of facing each other (refer to FIG. 3A). The real image R is acquired in the first imaging area G1 and the virtual image M (mirror image) is acquired in the second imaging area G2.

Although not illustrated, when the rear side of the choroid in the fundus center area is formed at the front side of the zero delay position Z (choroid mode), each of the tomographic images formed in the first imaging area G and in the second imaging area G2 is in a state of facing opposite direction from each other. The virtual image M is acquired in the first imaging area G1 and the real image R is acquired in the second imaging area G2.

For example, the controller 70 may extract any one of the image data of the first imaging area G1 or of the second imaging area G2 in the OCT data, and may display an image shown by the extracted image data on the screen of the display unit 75 (refer to FIG. 3B). As a result thereof, for example, only the real image R is displayed on the display unit 75, and the virtual image M is not displayed. In this way, for example, the examiner can observe the tomographic image of the fundus center area as a single tomographic image. As the OCT data of the fundus center area, for example, the OCT data including at least one of macula and papilla may be acquired.

When the image data is extracted and displayed, for example, the controller 70 may cut the image data from the OCT data or may create new image data from information corresponding to the image data.

FIG. 4A is a diagram illustrating an example of OCT data acquired in the second imaging mode, and FIG. 4B is a diagram illustrating an example of the OCT data obtained in the second imaging mode output on the display unit. In this case, for example, the controller 70 may adjust the difference in optical path length between the measurement light and the reference light such that the retinal surface in the fundus center area is formed at the inner side of the zero delay position Z and such that the rear side of the choroid in the fundus peripheral area is formed at the front side of the zero delay position Z.

In at least a part of the OCT data of the fundus center area, each of the tomographic images formed in the first and second image areas is in a state of facing each other. The real image R is acquired in the first imaging area G1 and the virtual image M (mirror image) is acquired in the second imaging area G2.

In at least a part of the OCT data in the fundus peripheral area, each of the tomographic images formed in the first imaging area and the second imaging area are in a state of facing the opposite direction. The virtual image M is acquired in the first imaging area G1 and the real image R is acquired in the second imaging area G2.

The fundus center area and the fundus peripheral area are relative and boundaries are not clearly defined, however, at least the area including both end portions in the OCT data of the fundus peripheral area is in a state of facing the opposite direction. In this case, a portion of the OCT data of the fundus peripheral area (the fundus center area side) can be in a state of facing each other.

For example, the controller 70 may extract the image data of both the first imaging area G1 and the second imaging area G2 in the OCT data, and may display an image shown by the extracted image data on the screen of the display unit 75. As a result thereof, for example, the tomographic image of the wide-angle region including the fundus center area and the fundus peripheral area is displayed on the display unit 75. In this way, for example, the examiner can observe the tomographic image of the wide-angle region of the fundus. In this case, for example, both the real image R and the virtual image M are displayed, however, the tomographic images intersect at only a partial portion and the intersection is made around the fundus where the retinal thickness is thin, and thus, the impact on the observation is not so significant. In addition, the image quality of one image can be low sensitivity and low resolution image by the dispersion correction by the software described above, it becomes easy to observe the other image.

In the OCT data on the wide-angle region, for example, the OCT data including the macula and the papilla may be acquired as the OCT data of the fundus center area, and for example, the OCT data of a peripheral region rather than the macula and the papilla may be acquired as the OCT data of the fundus peripheral area. In this case, at least a part of the OCT data of the peripheral region is acquired as the image data in the second imaging area.

In the description above, if the display state on the display unit is switched between the first imaging mode and the second imaging mode, the controller 70 may switch the display state when displaying the OCT data with a moving image as a live image. In this case, the OCT data may be displayed together with a fundus front image, and a graphic (for example, a line) indicating the scanning range may be displayed on the fundus front image. In addition, when the OCT data is displayed as a still image after acquiring the OCT data as a capture image, the controller 70 may switch the display state.

When storing the OCT data acquired as the capture image in the memory 72, the controller 70 may store the OCT data in the memory 72 in association with the imaging mode. In this way, when viewing the OCT data with the viewer software also, the controller 70 can switch the display state according to the imaging mode. Since the display state of the display unit 75 is switched according to the imaging mode, the controller 70 may store the OCT data in association with the display state of the display unit 75 when the capture operation is performed.

<Switching of Analysis Processing of OCT Data according to Imaging Mode>

The controller 70 may perform the analysis processing on the acquired OCT data to obtain an analysis result. For example, the controller 70 may perform segmentation processing on the OCT data and may obtain a layer thickness or a curvature of the retina or the choroid as an analysis result. In addition, if the OCT data is OCT motion contrast data (OCT angio data), analysis processing may be performed on the OCT motion contrast data to obtain the blood vessel density as an analysis result. The analysis result may be output to the display unit 75 and may be displayed, for example, as a numerical value or as an analysis map or an analysis chart.

In the analysis processing, for example, the controller 70 may change the analysis range of OCT data according to the imaging mode. When the imaging mode is set as the first imaging mode, the controller 70 may set the analysis range of the OCT data in the depth direction as the first analysis range, and when the imaging mode is set as the second imaging mode, the controller 70 may set the analysis range of the OCT data in the depth direction as the second analysis range which is wider than the first analysis range. In this case, in the second analysis range, the analysis range may be set such that the analysis processing is performed on the wide-angle region including the fundus center area and the fundus peripheral area.

When analyzing the OCT data acquired in the first imaging mode, the controller 70 may analyze the image data in any one of the first imaging area G1 or the second imaging area G2 in the OCT data and may acquire the analysis result. As a result thereof, for example, the analysis result of the fundus center area is obtained. As a analysis result of the fundus center area, for example, an analysis result on at least one of the macula and the papilla may be obtained.

When analyzing the OCT data acquired in the second imaging mode, the controller 70 may analyze the image data in both the first imaging area G1 and the second imaging area G2 in the OCT data and may acquire the analysis result. In this case, at least the image data of the fundus center area obtained in the first imaging area G1 may be analyzed and the image data of the fundus peripheral area obtained in the second imaging area G2 may be analyzed. As a result thereof, for example, the analysis result of the wide-angle region including the fundus center area and the fundus peripheral area is obtained. As the analysis result of wide-angle region, the analysis result on the macula and the papilla and the analysis result on the area around the macula and the papilla may be obtained.

<Composition of OCT Data and Analysis Result>

The controller 70 may synthesize the OCT data on the fundus center area acquired in the first imaging mode and the OCT data on the wide-angle region acquired in the second imaging mode by image processing, and may obtain a composite OCT data. The acquired composite OCT data may be displayed on the display unit 75. The controller 70 may perform position matching between the data by performing the matching processing in a common data area (for example, the OCT data of the fundus center area). In addition, a deviation of the imaging magnification between the data may be adjusted. Regarding the OCT data on the fundus center area, the OCT data obtained in the first imaging mode may be used or may be synthesized so as to be prioritized in the weighted composition.

In this case, for example, the OCT data on the fundus center area acquired in the first imaging mode can be acquired in higher density than OCT data of the fundus center area included in the OCT data on the wide-angle region acquired in the second imaging mode (for example, because the imaging time is short). Therefore, since the composite OCT data is acquired as the OCT data of the wide-angle region including the OCT data of the fundus center area with excellent resolution, for example, the examiner can observe the region including the macula or the papilla of the optical nervous system with high accuracy, and it is possible to reliably observe the fundus disease in the fundus peripheral area.

The controller 70 integrate the analysis result of the fundus center area based on the OCT data acquired in the first imaging mode and the analysis result of the fundus peripheral area based on the OCT data on the wide-angle region acquired in the second imaging mode, and may acquire an integrated analysis result. The acquired integrated analysis result may be displayed on the display unit 75. In acquiring the integrated analysis result, the controller 70 may acquire the integrated analysis result by analyzing the composite OCT data described above. In addition, the controller 70 may separately analyze the OCT data acquired in the first imaging mode and the OCT data acquired in the second imaging mode, and then, may integrate each results of analysis.

<Complementary Processing for Overlapping Region of Real Image and Virtual Image>

Figure 5:
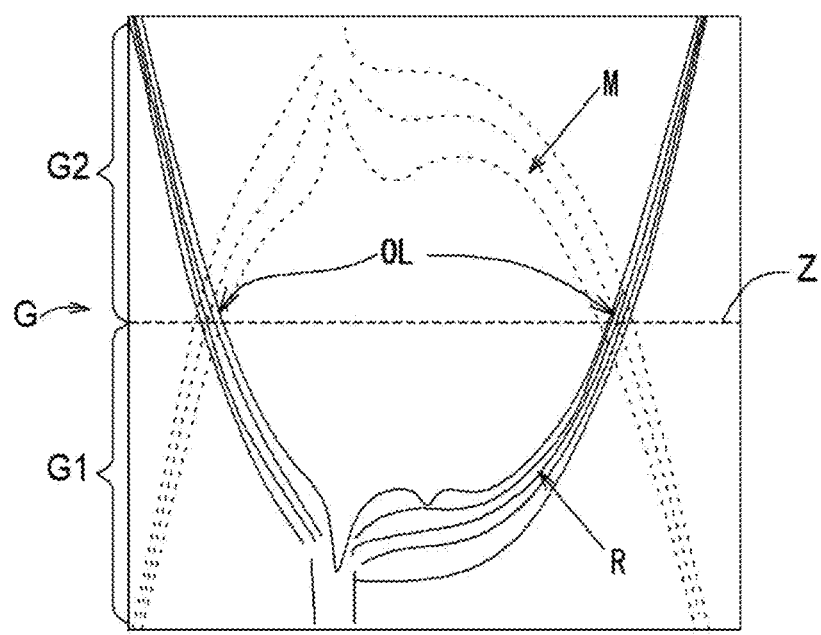
FIG. 5 is a diagram illustrating an overlapping region of a real image and a virtual image in the OCT data.

In a case where the OCT data in the wide-angle region is acquired in the second imaging mode, a real image R and a virtual image M in the OCT data overlap each other in the vicinity of a zero delay position Z as illustrated in FIG. 5. In other words, an overlapping region OL of the real image R and the virtual image M is generated in the OCT data. In the overlapping region OL, intensity data of the virtual image M is formed as a noise with respect to intensity data of the real image R, and thus, problems such as difficulty in observing a fundus tissue, difficulty in diagnosis, and difficulty in analysis can occur for an examiner.

Therefore, a control unit 70 may control an OCT optical system 100 to acquire a plurality of OCT data obtained with different optical path lengths when detecting a spectrum interference signal, and to perform the complementary processing on the overlapping region OL based on the plurality of OCT data.

Figure 6:
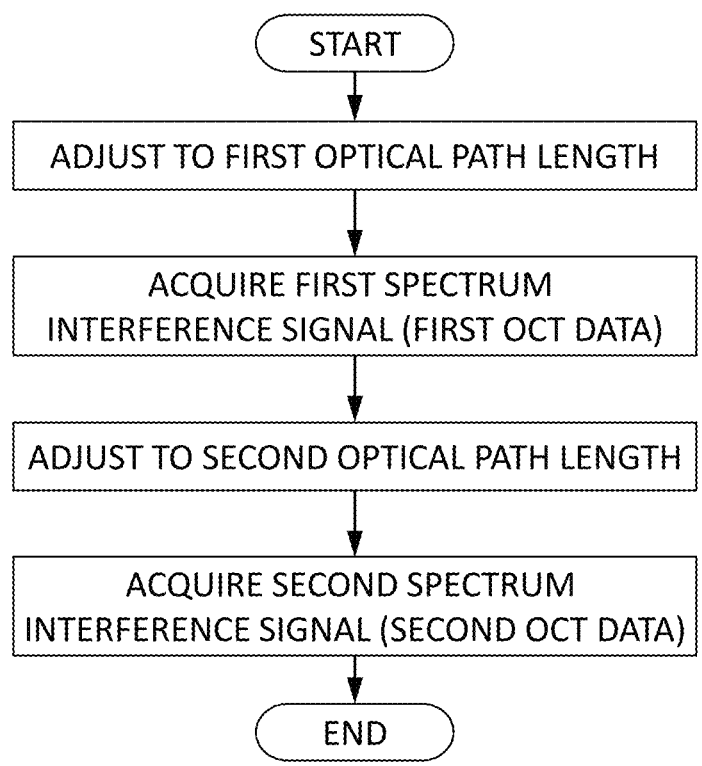
FIG. 6 is a flowchart illustrating an example of an apparatus control when obtaining a plurality of OCT data obtained with different optical path lengths.

FIG. 6 is a flowchart illustrating an example of an apparatus control when obtaining the plurality of OCT data obtained with different optical path lengths. For example, the control unit 70 may control an optical path length changing unit 200 to sequentially acquire the spectrum interference signal serving as a basis for the plurality of OCT data obtained with different optical path lengths. For example, a reference optical path adjusting unit 145 may be used, or a configuration in which a collimator lens 154 and a coupler of an optical fiber 152 are integrally moved may be used as the optical path length changing unit 200.

In this case, the control unit 70 controls a drive unit provided in the optical path length changing unit 200 to adjust the optical path length of the reference light (or measurement light) to the first optical path length. If a capture start signal is issued manually or automatically, the control unit 70 controls an optical scanner 156 to scan the measurement light on the fundus with the first optical path length, thereby, acquiring a first spectrum interference signal serving as a basis for the first OCT data. The control unit 70 can process the first spectrum interference signal to generate the first OCT data.

Next, the control unit 70 controls the drive unit provided in the optical path length changing unit 200 to automatically adjust the optical path length of the reference light (or measurement light) to the second optical path length different from the first optical path length. Thereby, a trouble of readjusting the optical path length can be reduced. The control unit 70 controls the optical scanner 156 to scan the measurement light on the fundus with the second optical path length, thereby, acquiring the second spectrum interference signal serving as a basis of the second OCT data. The control unit 70 can process the second spectrum interference signal to generate second OCT data.

In addition, likewise, the control unit 70 may control the optical path length changing unit 200 to acquire a spectrum interference signal serving as a basis of the third OCT data with a third optical path length different from the first optical path length and the second optical path length. Even in case of obtaining the spectrum interference signal after the fourth OCT data, the spectrum interference signal can be obtained by the same control.

FIG. 7 is an example of the plurality of OCT data at the same site having different optical path lengths, and FIG. 7 exemplified five OCT data, but the number of OCT data is not limited to this. Here, since the optical path lengths differ from each other when imaging is performed among each OCT data, a relative position of the virtual image M differs from the real image R. Then, a relative position of the overlapping region OL differs from the real image R among each OCT data.

In this case, for example, with respect to a portion influenced by the overlapping region OL in the first OCT data, since the relative positions of the overlapping region OL differ from each other after the second OCT data, a region not influenced by the overlapping region OL can be confirmed. That is, by acquiring the plurality of OCT data obtained with different optical path lengths, even if single OCT data is influenced by the overlapping region OL, other OCT data obtained with different optical path lengths are acquired, and thus, in an integrated manner, the good OCT data is obtained in which influence of the overlapping region OL is reduced.

Here, with respect to the portion influenced by the overlapping region OL in the first OCT data, the complementary processing is performed by using the OCT data of the same portion not influenced by the overlapping region OL after the second OCT data, and thus, the good OCT data is obtained in which the influence of the overlapping region OL is reduced.

FIG. 8 is a diagram illustrating an example of a case of removing the virtual image region prior to the complementary processing. The control unit 70 may detect the virtual image M by imaging processing on each OCT data and remove the virtual image M in advance. In case of detecting the virtual image M, the control unit 70 may detect the virtual image M through the imaging processing using a formation position of the virtual image M, signal intensity, sharpness, and the like.

For example, as a first method, in a case where the optical path length is adjusted such that the real image R of the OCT data at the fundus center area is formed in the first image region, since the virtual image M is formed in the second image region for the OCT data at the fundus center area, the control unit 70 may determine a region having a luminance level exceeding a predetermined threshold in the second image region as the virtual image M. Next, the control unit 70 generates a fitting curve configured by an approximate curve for a boundary portion with a background of the virtual image M obtained for the OCT data of the fundus center area. By doing so, the control unit 70 can detect the region of the virtual image M in the OCT data in the vicinity of the fundus by performing the fitting processing considering a shape (for example, the fundus has a curved shape) of a subject eye.

For example, the control unit 70 may use the fact that the real image R has a high definition and the virtual image M is blurred to determine the real image R and the virtual image M using the sharpness as a second method. In this case, the control unit 70 may detect a region having a luminance level exceeding a predetermined threshold in the OCT data through the imaging processing, detect the sharpness of the region exceeding the threshold, and detect a region including the blurred image data as the virtual image M. Here, in each A scan data, the control unit 70 may compare predetermined evaluation values (for example, (average maximum luminance value of image data)−(average luminance value of background region of image) between the first image region and the second image region, and set a higher evaluation value as the real image R and a lower evaluation value as the virtual image M. For example, contrasts of each A scan data may be used as the predetermined evaluation values.

Figure 9:
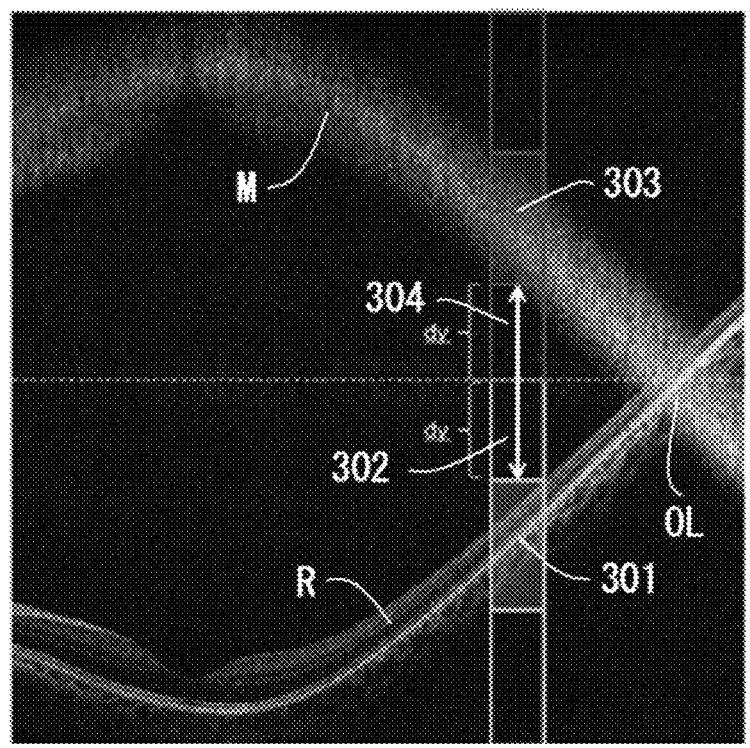
FIG. 9 is a diagram illustrating an example of a method of specifying a position of the virtual image.

FIG. 9 is a diagram illustrating an example of a method of specifying a position of a virtual image. For example, evaluation value=average luminance in region 301−average luminance in region 302+average luminance in region 303−average luminance in region 304 is used as an evaluation value for specifying the image position. Here, the control unit 70 changes dy in each A scan data and specifies a position where the evaluation value is maximum as an image position. Sizes of the region 301 and the region 303 may be set to a predetermined value in consideration of a thickness of a tissue (for example, fundus). Robustness can be achieved by using a symmetry between the real image and the virtual image. When an average luminance of each region is obtained, an integrated image obtained by integrating the luminance in the region in a depth direction may be used. In view of the region where the real image and the mirror image overlap each other, dy may be started from a negative value. FIG. 9 illustrates the regions 301 to 304 two-dimensionally for the sake of a convenient description, but in the present embodiment, the regions 301 to 304 are set for each A scan, and the regions 301 to 304 are set one-dimensionally.

If an image position is specified by using the evaluation value, the control unit 70 may compare signal intensities between the region 301 and the region 303, thereby, performing determination processing as to whether the image is a real image or a virtual image. In this case, the control unit 70 may compare the contrasts between the region 301 and the region 303 and determine a region having a lower contrast as the region including the virtual image M. Further, the control unit 70 may compares an evaluation value (for example, (average maximum luminance value of image data)−(average luminance value of background region of image)) between the region 301 and the region 303, and determine a region having a lower evaluation value as a region including the virtual image M.

In the above determination processing, a region where the real image R and the virtual image M overlap each other may also be determined as the region including the virtual image M. Since the evaluation values and the like between the region 301 and the region 303 are approximate in the overlapping region, in a case where the evaluation values and the like are approximate, the real image R and the virtual image M may be additionally determined as the overlapping region.

If a position of the virtual image M is specified by the determination processing, masking processing on a region corresponding to the virtual image M is performed, thereby, processing of erasing the virtual image M from the OCT data is performed (see, for example, FIG. 8). For example, processing of painting the region specified as the virtual image M with the same color as the background color (for example, black) may be performed as the masking processing. FIG. 8 illustrates the region subjected to the masking processing as a white image region for the sake of a convenient description.

FIG. 10 is a diagram illustrating an example in case of acquiring the addition average OCT data based on each OCT data. If the virtual image M is erased from each OCT data, the control unit 70 obtains positional deviation information between each OCT data and corrects a positional deviation between each OCT data based on the obtained positional information. The control unit 70 obtains the addition average OCT data by adding and averaging the corrected each OCT data.

Regarding the addition average OCT data, the region in which the virtual image M is erased in each OCT data is complemented by data relating to the same region of other OCT data. Thereby, a region where the real image and the virtual image of one OCT data overlap each other is replaced with good OCT data, and thereby, a wide range of good OCT data across the zero delay position can be obtained. Further, a noise is reduced by the average processing even in the entire OCT data, and thereby, good OCT data can be obtained. That is, the addition average processing is advantageous in that the complementary processing on the overlapping region and combination processing on the entire data can be performed in one processing.

Further, since the optical path lengths of each OCT data are different from each other, the image position for the zero delay position is different for each OCT data. By adding and averaging the OCT data, it is possible to obtain an image with uniform sensitivity in the entire OCT data.

Modification Example

Figure 11:
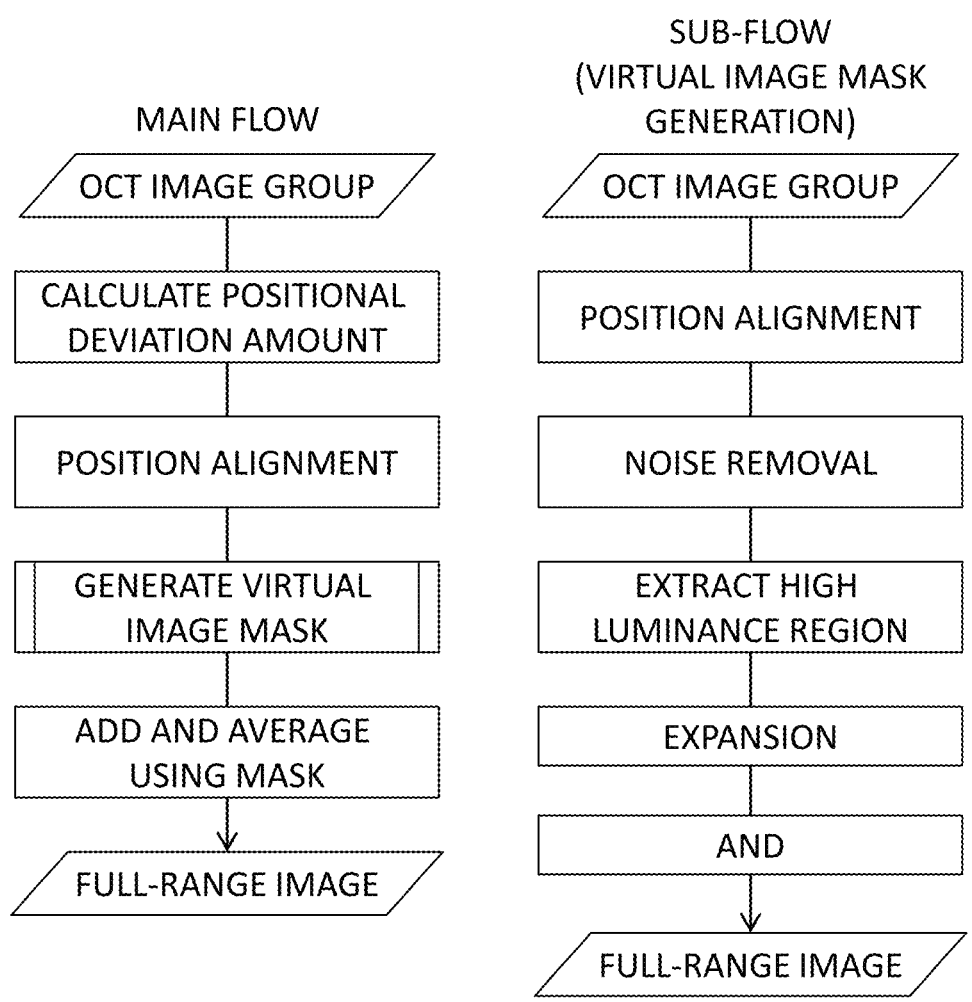
FIG. 11 is a flowchart illustrating an example of processing for detecting and erasing (excluding) a virtual image (mirror image) M.
Figure 12:
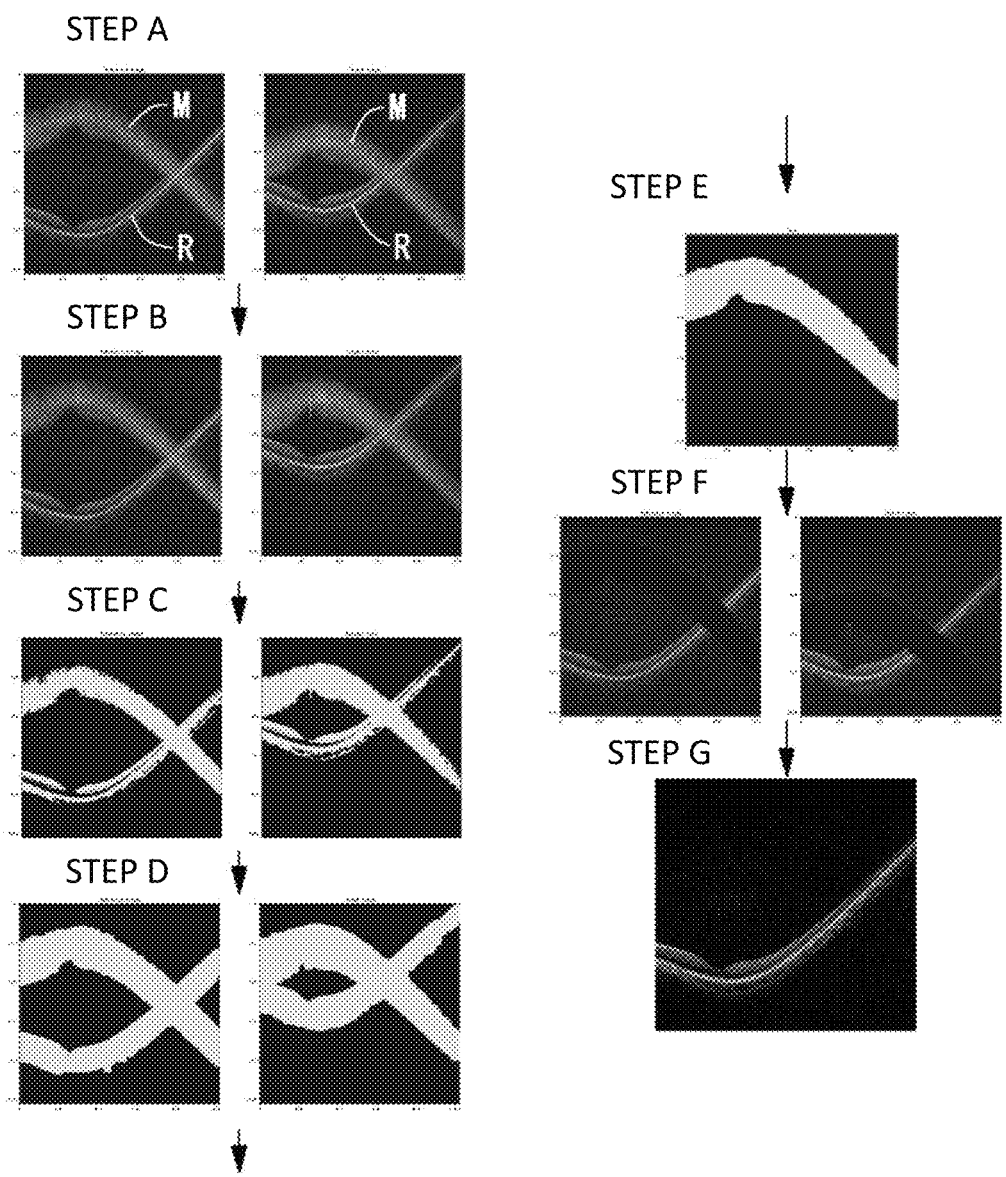
FIG. 12 is a diagram illustrating a progress relating to an example of processing for detecting and erasing the virtual image M.

FIG. 11 is a flowchart illustrating an example of processing for detecting and erasing (excluding) the virtual image (mirror image) M, and FIG. 12 is a diagram illustrating an example, which includes progress, of the processing for detecting and erasing the virtual image M. In case of detecting and erasing the virtual image M, the control unit 70 may include processing of matching the virtual images M between a plurality of OCT data at the same part having different optical path lengths.

In a main flow, the control unit 70 obtains positional deviation information (for example, positional deviation amount) between the real images R in each OCT data, and corrects a positional deviation between the real images R in each OCT data based on the obtained positional information. Thereby, positions of the real images R in each OCT data are matched (see, for example, positional deviation calculation amount and position alignment in FIG. 11, and step A in FIG. 12).

Next, the control unit 70 performs processing for generating a mask that erases a virtual image. In a sub-flow (virtual image mask generation flow), the control unit 70 corrects a positional deviation between the virtual images M in each OCT data by subtracting the positional deviation information (for example, the positional deviation amount) between the real images R. Thereby, positions of the virtual images M in each OCT data are matched (see, for example, step B of FIG. 12). Thereafter, the control unit 70 may perform noise removal (for example, speckle noise removal) using a Gaussian filter or the like.

The control unit 70 performs processing (for example, binarization processing) for extracting a high luminance region for each OCT data in which virtual images are matched (see, for example, to step C of FIG. 12). Thereby, for example, a region having a luminance exceeding a threshold is extracted, and thereby, regions corresponding to the real image R and the virtual image M are extracted in each OCT data.

The control unit 70 may perform expansion processing, which is a type of morphology processing, for each OCT data from which the high luminance region is extracted. (see, For example, step D of FIG. 12). Thereby, the high-luminance region is expanded, and thus, a variation when extracting a region corresponding to the virtual image M can be avoided.

Next, the control unit 70 receives each OCT data and takes a logical product (AND operation) for each pixel (for example, see step E in FIG. 12). In this case, since a region corresponding to the virtual image M matches on each OCT data, the virtual image M remains. Meanwhile, since regions corresponding to the real images R are different from each other on each OCT data, an AND operation is performed for luminance values of a background of each OCT data. As a result, the virtual image M remains and the real image R is erased. That is, the region corresponding to the virtual image M is detected based on a plurality of OCT data.

The control unit 70 generates the region corresponding to the virtual image M as a mask image, based on the detection result. The mask image is used to erase the virtual image M on each OCT data, and is generated, for example, as image data in which the region specified as the virtual image M is painted with the same color as a background color (for example, black).

If the virtual image mask is generated, the control unit 70 performs an addition average processing by using the generated mask (see, for example, main flow of FIG. 11). For example, the control unit 70 performs masking processing for erasing the virtual image M for each OCT data in which the real images are matched (see, for example, step F of FIG. 12). That is, the masking processing is performed for the region corresponding to the virtual image M on each OCT data.

In this case, a mask image generated in step E may be used, and the control unit 70 displaces the mask image by using positional deviation information (for example, positional deviation amount) between the real images R, thereby, a position of the virtual image M on each OCT data is matched with a position of the mask image. Furthermore, the control unit 70 performs the masking processing for the image data of the region overlapping the mask image on each OCT data. Thereby, the virtual image M is erased on each OCT data.

The control unit 70 adds and averages each OCT data in which the virtual image M is erased, thereby, acquiring addition average OCT data (see, for example, step G of FIG. 12). Thereby, the complementary processing is performed for the region where the real image and the virtual image overlap each other.

According to the above-described processing for matching the virtual images M, a region corresponding to the virtual image M is detected by using a plurality of OCT data, thereby, enabling the masking processing using the same mask for each OCT data. As a result, the processing of erasing the virtual image M from each OCT data can be accurately performed, and combined good OCT data is obtained.

Figure 13:
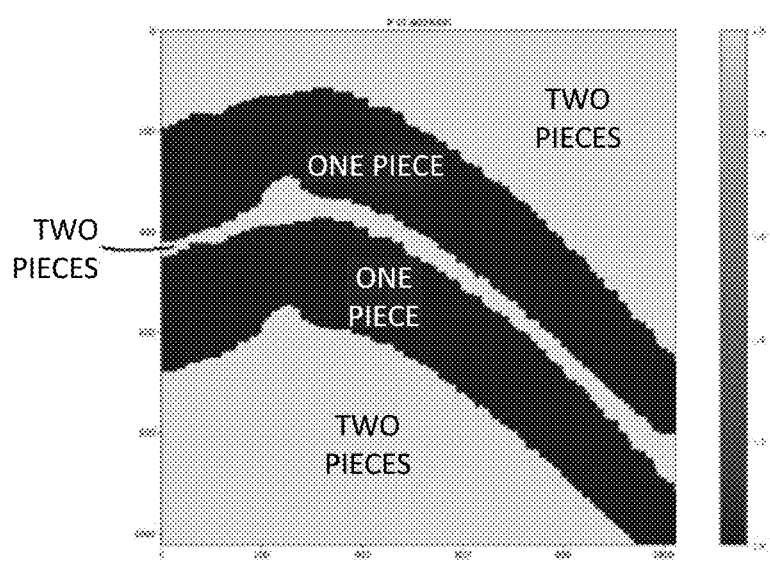
FIG. 13 is a diagram illustrating an example of a case where the number of added sheets is changed depending on presence and absence of masking processing.

In a case where average processing is performed, it is common that intensity values of each OCT data in pixel units are added and thereafter the added value is divided by the number of added pieces, but in this embodiment, the control unit 70 may not count the number of addition when dividing the added value for the region subjected to the masking processing (see, for example, FIG. 13). Thereby, in the OCT data after averaging, it is possible to reduce unevenness in a luminance level between the region erased by the masking processing and the region where the masking processing is not performed. For example, in a case where an addition average of two OCT data in which the virtual image M is erased by the masking processing is acquired, an addition value of the intensity values of each OCT data is divided by 1 for the region where the masking processing is performed. For a region that is not masked, an addition value of the intensity values of each OCT data is divided by two.

FIG. 14 is a diagram illustrating an example, which includes a progress, of processing of detecting and erasing the virtual image M. In case of detecting and erasing the virtual image M, the control unit 70 may include processing of matching the real images R between a plurality of OCT data at the same part having different optical path lengths.

The control unit 70 obtains positional deviation information (for example, positional deviation amount) between the real images R in each OCT data, and corrects a positional deviation between the real images R in each OCT data based on the obtained positional information. Thereby, positions of the real images R in each OCT data are matched (see, for example, step 1 of FIG. 14).

The control unit 70 compares each OCT data in which the real images are matched in pixel units, thereby, performs processing of adopting a minimum value of the luminance value as an image (see, for example, step 2 of FIG. 14). Hereinafter, an image obtained by the processing is referred to as a minimum value image. In this case, since a region corresponding to the real image R matches on each OCT data, the real image R remains even if the minimum value is adopted. Meanwhile, since regions corresponding to the virtual images M are different from each other on each OCT data, s luminance value of a background of each OCT data is adopted in a case where the minimum value is adopted. As a result, the real image R remains and the virtual image M is erased. That is, the region corresponding to the real image R is detected based on a plurality of OCT data. The minimum value image is used for defining a position of the real image R on each OCT data. However, the minimum value image may be used as the combined OCT data. A method of making the real image R remain and erasing the virtual image M is not limited to the method of adopting the minimum value of the luminance value as the image, and, for example, various statistics such as an average, a median value, and a most frequent value of the luminance values may be used.

The control unit 70 obtains a correlation between each OCT data and the minimum value image in pixel units, thereby, performing processing of acquiring a height of the correlation as an image (see, for example, step 3 of FIG. 14). Hereinafter, an image obtained by the processing is referred to as a correlation image. In this case, since the minimum value image defines a position of the real image R based on a plurality of OCT data, a region corresponding to the real image R in each OCT data has a high correlation value, and a region corresponding to the virtual image or the background has a low correlation value. As a result, the region corresponding to the real image R is detected in the correlation image of each OCT data.

The control unit 70 adds and averages each OCT data in which the real images are matched, thereby, acquiring the addition average OCT data (see, for example, step 4 of FIG. 14). In this case, the control unit 70 may perform weighting when adding each OCT data by using the above-described correlation image.

For example, when adding the OCT data in pixel units, the control unit 70 may increase the weighting coefficient at the time of addition in a pixel with a high correlation in each OCT data, and may reduce the weighting coefficient at the time of addition in a pixel with a low correlation. In this case, the weighting coefficient is set for each OCT data in pixel units.

According to the above-described processing of matching the real images R, a region corresponding to the real image R is detected by using a plurality of OCT data, and a correlation is obtained for each OCT data by using the same image (for example, a correlation image). Furthermore, weighting addition is performed by using the obtained correlation result, and thereby, the virtual image M can be erased from the OCT data. As a result, the processing of erasing the virtual image M can be performed with a high accuracy, and thereby, good combined OCT data is obtained.

In the above description, the control unit 70 performs weighting addition by using a correlation result with a region corresponding to the real image R detected in advance, but the present invention is not limited to this, and for example, the control unit 70 may perform the weighting addition by using a correlation result with a region (see, for example, FIG. 12) corresponding to the virtual image M detected in advance. In this case, a pixel with a high correlation with the virtual image M has a small weighting coefficient at the time of addition, and a pixel with a low correlation has a large weighting coefficient at the time of addition. The control unit 70 may use both the weighting addition using the correlation with the region corresponding to the real image R and the weighting addition using the correlation with the region corresponding to the virtual image M. Further, a method of separating the real image and the virtual image is not limited to the above-described method, and a statistical analysis such as robust PCA may be used.

Although an example of removing the virtual image M is illustrated in the above-described example, the present invention is not limited to this, and for a region where the real image R and the virtual image M overlap each other, the virtual image M may not necessarily be removed in processing of complementing to good OCT data in which the real image R and the virtual image M do not overlap. For example, only by processing of adding and averaging a plurality of OCT data obtained with different optical path lengths, an influence of the virtual image in the region where the real image and the virtual image overlap is reduced.

A method of generating combined OCT data based on a representative value of a plurality of OCT data without being limited to the complementary processing by addition averaging processing may use, for example, a median value or a most frequent value of the plurality of OCT data.

The method of the complementary processing is not limited to the method of obtaining the representative value of the OCT data, and for example, after OCT data of an overlapping region in the one OCT data is removed, OCT data in the same region as the overlapping region may be replaced with the other OCT data and combined for the removed part. In this case, a positional relationship may be associated by processing of matching the one OCT data and the other OCT data.

The control unit 70 may perform at least one of complementary processing relating to an overlapping region of a real image and a virtual image and removal processing relating to the virtual image based on an operation signal from an operation unit operated by an examiner. Thereby, selective processing can be performed.

In the above description, an example is taken in which an OCT apparatus for imaging a subject eye at a wide angle, but the present invention is not limited to this, and the present embodiment may be applied to the OCT apparatus for imaging the OCT data of an object to be examined at a wide angle. The object to be examined may be, for example, a living body such as an eye (front eye portion, fundus, or the like) and skin, or a material other than the living body.

What is claimed is:

1. An OCT apparatus comprising:
   an OCT optical system that has a light splitter splitting light from an OCT light source to light travelling a measurement light path and light travelling to a reference light path, and a detector detecting a spectrum interference signal of measurement light guided to a subject eye through the measurement light path and reference light from the reference light path; and
   a processor that processes the spectrum interference signal to generate OCT data,
   wherein the processor performs at least complementary processing on an overlapping region of a real image and a virtual image in OCT data based on a plurality of OCT data obtained with different optical path lengths when detecting the spectrum interference signal, and generates OCT data subjected to the complementary processing.

2. The OCT apparatus according to claim 1, further comprising:
   an optical path length adjuster that change an optical path length of at least one of the measurement light path and the reference light path,
   wherein the processor controls the optical path length adjuster to sequentially acquires the spectrum interference signals serving as a basis of the plurality of OCT data obtained with the different optical path lengths.

3. The OCT apparatus according to claim 2, further comprising:
   an optical scanner that scans the measurement light guided to the subject eye on the subject eye,
   wherein the processor controls the optical scanner and the optical path length adjuster to perform:
   a first scanning control of scanning the measurement light on each of a plurality of scanning lines with a first optical path length, and
   a second scanning control of scanning the measurement light on each of a plurality of scanning lines with a second optical path length different from the first optical path length after the first scanning control is performed.

4. The OCT apparatus according to claim 1,
   wherein the processor generates combined OCT data based on a representative value of the plurality of OCT data as the complementary processing.

5. The OCT apparatus according to claim 1,
   wherein the processor replaces data of the overlapping region of the real image and the virtual image in OCT data with other OCT data in which the real image and the virtual image overlap in a region different from the overlapping region as the complementary processing.

6. The OCT apparatus according to claim 1,
   wherein the processor performs matching processing for correcting a positional deviation between the plurality of OCT data obtained with the different optical path lengths.

7. The OCT apparatus according to claim 1,
   wherein the processor detects either of a real image region and a virtual image region in OCT data, and performs the complementary processing with excluding OCT data of the detected region.

8. The OCT apparatus according to claim 1,
   wherein the processor enables to output OCT data generated by processing the spectrum interference signal to a display, and switches a display state of the display between a first imaging mode for obtaining OCT data at a fundus center area of the subject eye and a second imaging mode for obtaining OCT data on a wide-angle region including the fundus center area and a fundus peripheral area of the subject eye, and
   in a case where the second imaging mode is set, the processor outputs both front and rear image regions with respect to a zero delay position on OCT data to the display, and outputs OCT data in which the complementary processing is performed to the display.

* * * * *